United States Patent
Purcell et al.

(10) Patent No.: US 10,314,904 B2
(45) Date of Patent: Jun. 11, 2019

(54) METHODS FOR ENHANCING EFFICACY OF A VACCINE BY ADMINISTERING AN IL-4R ANTAGONIST

(71) Applicant: Regeneron Pharmaceuticals, Inc., Tarrytown, NY (US)

(72) Inventors: Lisa Purcell, Garnerville, NY (US); Neil Graham, Croton-on-Hudson, NY (US); Andrew J. Murphy, Croton-on-Hudson, NY (US); Robert Evans, Cambridge, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/436,032

(22) Filed: Feb. 17, 2017

(65) Prior Publication Data
US 2017/0239342 A1 Aug. 24, 2017

Related U.S. Application Data

(60) Provisional application No. 62/297,257, filed on Feb. 19, 2016, provisional application No. 62/409,936, filed on Oct. 19, 2016.

(51) Int. Cl.
| A61K 39/00 | (2006.01) |
| A61K 39/02 | (2006.01) |
| C07K 16/28 | (2006.01) |
| A61K 39/395 | (2006.01) |
| C07K 16/12 | (2006.01) |

(52) U.S. Cl.
CPC .......... *A61K 39/099* (2013.01); *A61K 39/395* (2013.01); *A61K 39/3955* (2013.01); *C07K 16/1225* (2013.01); *C07K 16/28* (2013.01); *C07K 16/2866* (2013.01); *A61K 2039/505* (2013.01); *A61K 2039/54* (2013.01); *A61K 2039/545* (2013.01); *A61K 2039/55* (2013.01); *A61K 2039/55505* (2013.01); *A61K 2039/57* (2013.01); *A61K 2039/622* (2013.01); *C07K 2317/21* (2013.01); *C07K 2317/565* (2013.01); *C07K 2317/70* (2013.01); *C07K 2317/76* (2013.01); *Y02A 50/388* (2018.01); *Y02A 50/407* (2018.01); *Y02A 50/412* (2018.01); *Y02A 50/466* (2018.01); *Y02A 50/484* (2018.01)

(58) Field of Classification Search
None
See application file for complete search history.

(56) References Cited

U.S. PATENT DOCUMENTS

| 7,186,809 | B2 | 3/2007 | Pluenneke |
| 7,465,450 | B2 | 12/2008 | Pluenneke |
| 7,605,237 | B2 | 10/2009 | Stevens et al. |
| 7,608,693 | B2 | 10/2009 | Martin et al. |
| 7,638,606 | B2 | 12/2009 | Carter et al. |
| 7,794,717 | B2 | 9/2010 | Stevens et al. |
| 8,092,804 | B2 | 1/2012 | Eriksson et al. |
| 8,679,487 | B2 | 3/2014 | Armitage et al. |
| 8,877,189 | B2 | 11/2014 | Eriksson et al. |
| 2009/0074793 | A1* | 3/2009 | Martin ............... C07K 16/2866 424/172.1 |
| 2014/0072583 | A1 | 3/2014 | Ardeleanu et al. |
| 2014/0356372 | A1 | 12/2014 | Stahl et al. |
| 2015/0017182 | A1* | 1/2015 | Mannent ............ A61K 39/3955 424/158.1 |

FOREIGN PATENT DOCUMENTS

| EP | 2245064 B1 | 7/2014 |
| WO | WO 09/081201 A2 | 7/2009 |
| WO | 10/120511 A2 | 10/2010 |
| WO | 13/181696 A1 | 12/2013 |
| WO | 14/039461 A1 | 3/2014 |
| WO | 14/197470 A1 | 12/2014 |

OTHER PUBLICATIONS

U.S. Appl. No. 62/297,257, filed Feb. 19, 2016, Expired.
U.S. Appl. No. 62/409,936, filed Oct. 19, 2016, Pending.
PCT/US2017/018487, Feb. 17, 2017, Pending.
WIPO Application No. PCT/US2017/018487, PCT International Search Report and Written Opinion of the International Searching Authority dated May 10, 2017.
Allen et al., "Improved pertussis vaccines based on adjuvants that induce cell-mediated immunity," Expert Rvw. Vaccines, 13(10):1253-1264, (2014).
Bancroft et al., "Th1 versus Th2 T cell polarization by whole-cell and acellular childhood pertussis vaccines persists upon re-immunization in adolescence and adulthood," Cellular Immunology, 304-305:35-43, (2016).
Brummelman et al., "Roads to the development of improved pertussis vaccines paved by immunology," FEMS Pathogens and Disease, 73(8):ftv067, 12 pages, doi: 10.1093/femspd/ftv067, (2015).
Dipasquale et al., "Vaccine Adjuvants: from 19 20 to2015 and Beyond,"Vaccines, 3:320-343, doi:10.339 0/vaccines3020320, (2015).
Dunne et al., "A novel TLR2 agonist from Bordetella pertussis is a potent adjuvant that promotes protective immunity with an acellular pertussis vaccine," Publication, 8(3):607-617, doi:10.1038/mi.2014. 93, (2015). Published online Oct. 15, 2014.

(Continued)

*Primary Examiner* — Jana A Hines
*Assistant Examiner* — Khatol S Shahnan Shah
(74) *Attorney, Agent, or Firm* — Schwabe, Williamson & Wyatt PC; Aparna G. Patankar

(57) ABSTRACT

The present invention provides methods for enhancing the efficacy and/or safety of a vaccine. In certain embodiments, the invention provides methods to increase or potentiate the immune response to a vaccine in a subject in need thereof. The methods of the present invention comprise administering to a subject in need thereof an interleukin-4 receptor (IL-4R) antagonist such as an anti-IL-4R antibody in combination with said vaccine. In certain embodiments, the methods of the present invention are used to afford enhanced protection to an infectious disease such as whooping cough.

21 Claims, 10 Drawing Sheets
Specification includes a Sequence Listing.

(56) References Cited

OTHER PUBLICATIONS

Garlapati, "Do we know the Th1/Th2/Th17 determinants of vaccine response?" Expert Rvw. Vaccines, 11(11):1307-1310, (2012).
Kovarik et al., "Optimization of vaccine responses in early life: The role of delivery systems and immunomodulators," Immunology and Cell Biology, 76:222-236, (1998).
Mills et al., "Do we need a new vaccine to control the re-emergence of pertussis?," Trends in Microbiology, 22(2):49-52, (2014).
Mills et al., "Mouse and Pig Models for Studies of Natural and Vaccine-Induced Immunity to Bordetella pertussis," JID, 209(Suppl 1):S16-S19, (2014).
Ross et al. Relative Contribution of Th1 and Th17 Cells in Adaptive Immunity to Bordetella pertussis: Towards the Rational Design of an Improved Acellular Pertussi Vaccine, PLoS Pathog, 9(4):e1003264, 14 pages, doi:10.1371/journal.ppat.1003264, (2013).
Siegrist, "Vaccine immunology." Vaccines, pp. 17-36, (2008).
Warfel et al., "Accellular pertussis vaccines protect against disease but fail to prevent infection and transmission in a nonhuman primate model," PNAS, 111(2):787-792, (2014).

\* cited by examiner

Figure 1 aP or wP vaccine, i.p. ⅕ human dose

α-IL-4Rα or isotype control, dosed s.c. weekly (25 mg/kg)

Aerosolized B. pertussis challenge

Sample collection

METHODS FOR ENHANCING EFFICACY OF A VACCINE BY ADMINISTERING AN IL-4R ANTAGONIST

CROSS-REFERENCE TO RELATED APPLICATIONS

This application claims the benefit under 35 U.S.C. § 119(e) of U.S. provisional application No. 62/297,257, filed on Feb. 19, 2016; and 62/409,936, filed on Oct. 19, 2016, the disclosures of which are each herein incorporated by reference in their entireties.

REFERENCE TO A SEQUENCE LISTING

This application incorporates by reference the Sequence Listing submitted in computer readable form as file 10209US01-Sequence.txt, created on Feb. 10, 2017, and containing 15,360 bytes.

FIELD OF THE INVENTION

The present invention relates to methods for increasing the efficacy of a vaccine. More specifically, the invention relates to the administration of an interleukin-4 receptor (IL-4R) antagonist in combination with a vaccine in a subject in need thereof.

BACKGROUND

Vaccines have been one of the most successful public health interventions in preventing disease and death due to infectious disease. Vaccines typically contain the causative agent of a disease, its products or its substitute which acts as an antigen without causing the disease (or causing mild disease, in some cases). Some current vaccines against, e.g., microbial pathogens, consist of live attenuated or non-virulent variant strains of microorganisms, or killed or otherwise inactivated organisms. Other vaccines utilize more or less purified components of pathogen lysates such as surface carbohydrates, recombinant pathogen-derived proteins that are sometimes fused to other molecules, or replicative viruses that produce an antigen from a pathogen. Vaccines work by inducing an endogenous immune response resulting in the activation of antigen-specific naive lymphocytes that then give rise to antibody-secreting B cells or antigen-specific effector and memory T cells or both. This approach can result in long-lived protective immunity that may be boosted from time to time by renewed exposure to the same antigenic material.

Vaccines commonly contain adjuvants that help to accelerate, prolong and/or enhance antigen-specific immune responses. Some commonly used adjuvants include, but are not limited to, aluminium salts (e.g., alum, aluminium phosphate, and aluminium hydroxide), Freund's complete adjuvant, Freund's incomplete adjuvant, Ribi's adjuvant, squalene, and MF59®.

There remains a need for safe and effective vaccines and/or for improved vaccination strategies to enhance efficacy and to provide more durable protection to pathogen exposure and challenge, without any adverse side effects (e.g., an allergic reaction).

BRIEF SUMMARY OF THE INVENTION

According to certain aspects of the present invention, methods are provided for enhancing the efficacy and/or safety of a vaccine in a subject. Also included are methods for increasing the immune response against a vaccine or for increasing the duration of protective immunity of a vaccine in a subject. In certain embodiments, the present invention provides methods for increasing protection against a disease in a subject and/or for preventing infection and transmission of said disease to an uninfected subject or for preventing progression of the disease to another disease. The methods, according to these aspects, comprise administering to a subject in need thereof an interleukin-4 receptor (IL-4R) antagonist in combination with a vaccine. In certain embodiments, the methods comprise selecting a subject that is susceptible to a microbial infection and administering to the subject in need thereof an interleukin-4 receptor (IL-4R) antagonist in combination with a vaccine against said microbial infection. In certain embodiments, the IL-4R antagonist is administered before, after or concurrent with a vaccine in a subject in need thereof.

According to certain aspects, the present invention provides for methods for preventing, treating, reducing or ameliorating an adverse side effect (e.g., an allergic reaction) of a vaccine in a subject in need thereof. In certain embodiments, the present invention provides methods for preventing, reducing or ameliorating T helper 2 (Th2) response elicited by a vaccine in a subject in need thereof. In certain embodiments, the present invention provides methods for reducing IgE induced by a vaccine in a subject in need thereof. The methods, according to these aspects, comprise administering an IL-4R antagonist in combination with a vaccine to a subject in need thereof.

According to certain aspects, the present invention provides methods to reduce the number of vaccine doses, the methods comprising administering an IL-4R antagonist in combination with said vaccine to a subject in need thereof. In certain embodiments, the number of vaccine doses is reduced by one or more doses, e.g., by one dose, by two doses, or more as compared to a subject not administered an IL-4R antagonist.

According to certain aspects, the present invention provides methods for treating atopic dermatitis in a patient without interfering with the patient's response to a vaccine. In certain embodiments, the present invention provides methods for treating atopic dermatitis in a patient without suppressing the patient's response to a vaccine. The methods, according to these aspects, comprise selecting a patient diagnosed with atopic dermatitis who has recently been or will be inoculated with a vaccine; and administering to the patient one or more doses of an IL-4R antagonist, wherein the IL-4R antagonist does not reduce or attenuate the patient's response to the vaccine. In certain embodiments, the administration of the IL-4R antagonist results in an improvement in one or more atopic dermatitis (AD)-related parameters selected from the group consisting of Investigators Global Assessment (IGA); Body Surface Area Involvement of Atopic Dermatitis (BSA); Eczema Area and Severity Index (EASI); Scoring atopic dermatitis (SCORAD); 5-D Pruritus Scale; and Pruritus Numeric Rating Scale (NRS). In certain embodiments, the patient with atopic dermatitis is susceptible to a microbial infection, e.g., pertussis, diphtheria, tetanus, tuberculosis, meningitis, etc. In certain embodiments, the patient with atopic dermatitis is allergic to certain components of a vaccine or develops allergic reaction (e.g., skin reaction) to a vaccine. In certain embodiments, the patient is a child less than about 3 years of age that has been diagnosed with atopic dermatitis and is need of a vaccine against an infectious disease (e.g., pertussis).

In certain embodiments, the vaccine is against a disease or infection caused by a microbe selected from the group consisting of *Bordetella pertussis, Corynebacterium diptheriae, Clostridium tetani, Mycobacterium tuberculosis, Plasmodium* spp., *Bacillus anthracis, Vibrio cholera, Salmonella typhi, Borrelia* spp., *Streptococus pneumoniae, Staphylococcus aureus, Escherichia coli, Clostridium* spp., *Mycobacterium leprae, Yersinia pestis*, influenza virus, varicella zoster virus, human immunodeficiency virus (HIV), respiratory syncytial virus (RSV), polio virus, variola virus, rabies virus, rotavirus, human papillomavirus, Ebola virus, hepatitis A virus, hepatitis B virus, hepatitis C virus, lyssavirus, measles virus, mumps virus, and Rubella virus.

In certain embodiments, the vaccine is against a disease or infection selected from the group consisting of pertussis, diphtheria, tetanus, tuberculosis, malaria, anthrax, cholera, typhoid, leprosy, Lyme's disease, streptococcal infection, *E. coli* infection, staphylococcal infection, plague, clostridial infection, meningococcal infection, pneumococcal infection, pneumonia, meningitis, sepsis, influenza, chickenpox, HIV infection, RSV infection, polio, small pox, rabies, rotavirus infection, papillomas, cervical cancer, Ebola, hepatitis, yellow fever, measles, mumps and Rubella infection. In one embodiment, the vaccine is against pertussis (whooping cough).

According to certain embodiments, the methods of the present invention comprise administering one or more doses of an IL-4R antagonist in combination with one or more doses of a vaccine to a subject in need thereof. In certain embodiments, one or more doses of an IL-4R antagonist are administered wherein each dose is administered 1-12 weeks after the immediately preceding dose. In certain embodiments, each dose of the IL-4R antagonist comprises 1-50 mg/kg of the subject's body weight. In certain embodiments, each dose of the IL-4R antagonist comprises 10-600 mg of the IL-4R antagonist. In certain embodiments, each dose comprises 0.1 to 10 mg/kg of the subject's body weight. In certain embodiments, one or more doses of a vaccine are administered wherein each dose is administered 2-24 months after the immediately preceding dose. In certain embodiments, one or more doses of a vaccine are administered at an interval of 2-15 years after the immediately preceding dose. In certain embodiments, the subsequent doses of a vaccine are referred to as 'booster' doses. In certain embodiments, the methods comprise administering one or more doses of the IL-4R antagonist before each dose of the vaccine followed by administering a dose of the IL-4R antagonist concurrent with a dose of the vaccine. In a further embodiment, the methods comprise optionally administering one or more doses of the IL-4R antagonist after administering a dose of the vaccine.

In certain embodiments, the methods of the present invention comprise administering about 10 mg to about 600 mg of an IL-4R antagonist as an initial dose followed by one or more secondary doses. In certain embodiments, the initial dose and the one or more secondary doses each comprise about 10 mg to about 600 mg of the IL-4R antagonist. In certain embodiments, the IL-4R antagonist is administered at an initial dose of 600 mg followed by one or more secondary doses wherein each secondary dose comprises 300 mg. In one embodiment, the IL-4R antagonist is administered at an initial dose of 400 mg followed by one or more secondary doses wherein each secondary dose comprises 200 mg. In certain embodiments, the initial and one or more secondary doses each comprise 0.1 to 10 mg/kg of the IL-4R antagonist. In certain embodiments, the initial and one or more secondary doses each comprise 1, 2, 3, 5, or 6 mg/kg of the IL-4R antagonist. According to this aspect of the invention, the IL-4R antagonist may be administered to the subject at a dosing frequency of, e.g., once a week, once in 2 weeks, once in 3 weeks or once in 4 weeks. In one embodiment, each secondary dose is administered 1 week after the immediately preceding dose. In certain embodiments, the vaccine is administered at an initial dose followed by one or more subsequent (booster) doses wherein each subsequent (booster) dose is administered 1-104 weeks after the immediately preceding dose. In certain embodiments, one or more subsequent (booster) doses are administered 2-20 years after the immediately preceding dose.

In certain embodiments, the IL-4R antagonist is administered before, after or concurrent with a vaccine in a subject in need thereof. In certain embodiments, one or more doses of the IL-4R antagonist are administered before, after or concurrent with each dose of the vaccine. In certain embodiments, one or more doses of the IL-4R antagonist are administered before each dose of the vaccine. In certain embodiments, one or more doses of the IL-4R antagonist are administered after each dose of the vaccine. In certain embodiments, one or more doses of the IL-4R antagonist are administered before a dose of the vaccine, followed by a dose of the IL-4R antagonist concurrent with a dose of the vaccine, optionally followed by one or more doses of the IL-4R antagonist after the vaccine administration.

According to certain aspects, the present invention provides vaccination regimens in a subject comprising administration of an initial dose of a vaccine, optionally, followed by one or more subsequent booster doses, wherein the administration of each vaccine dose comprises administration of one or more doses of an IL-4R antagonist followed by a dose of the IL-4R antagonist with said vaccine followed by one or more doses of the IL-4R antagonist. In certain embodiments, the one or more doses of the IL-4R antagonist are administered at an interval of once a week, once in 2 weeks, once in 3 weeks, or once in 4 weeks after the immediately preceding dose.

Exemplary IL-4R antagonists that can be used in the context of the methods of the present invention include, e.g., small molecule chemical inhibitors of IL-4R or its ligands (IL-4 and/or IL-13), or biological agents that target IL-4R or its ligands. According to certain embodiments, the IL-4R antagonist is an antigen-binding protein (e.g., antibody or antigen-binding fragment thereof) that binds the IL-4Rα chain and blocks signaling by IL-4, IL-13, or both IL-4 and IL-13. In one embodiment, the antibody or antigen-binding fragment thereof that specifically binds IL-4R comprises complementarity determining regions (CDRs) in a heavy chain variable region (HCVR)/light chain variable region (LCVR) sequence pair of SEQ ID NOs: 1/2. In certain embodiments, the antibody or antigen-binding fragment thereof comprises a heavy chain CDR (HCDR1) having amino acid sequence of SEQ ID NO: 3, a HCDR2 having amino acid sequence of SEQ ID NO: 4, a HCDR3 having amino acid sequence of SEQ ID NO: 5, a light chain CDR (LCDR1) having amino acid sequence of SEQ ID NO: 6, a LCDR2 having amino acid sequence of SEQ ID NO: 7, and a LCDR3 having amino acid sequence of SEQ ID NO: 8. One such type of antigen-binding protein that can be used in the context of the methods of the present invention is an anti-IL-4Rα antibody such as dupilumab.

In some embodiments, the IL-4R antagonist is administered subcutaneously, intravenously, or intraperitoneally to the subject.

According to certain aspects, the present invention provides vaccine compositions comprising an adjuvant, wherein the adjuvant comprises an IL-4R antagonist. In certain embodiments, the vaccine composition further comprises a vaccine component selected from the group consisting of tetanus toxoid, diphtheria toxoid, inactivated pertussis toxin, filamentous hemagglutinin, pertactin, fimbriae type 2, fimbriae type 3, and formalin-inactivated respiratory syncytial virus. In certain embodiments, the vaccine composition comprises a second adjuvant (e.g., alum).

In certain embodiments, the present invention provides use of an IL-4R antagonist of the invention in the manufacture of a medicament to enhance efficacy and/or safety of a vaccine in a patient. In certain embodiments, the present invention provides use of an IL-4R antagonist in a method to increase the efficacy and/or safety of a vaccine, wherein the IL-4R antagonist is administered in combination with said vaccine to a subject in need thereof.

Other embodiments of the present invention will become apparent from a review of the ensuing detailed description.

BRIEF DESCRIPTION OF THE FIGURES

FIG. 1 shows the study design including dosing and sample collection schedule for the study in Example 1, 2, 3, or 4.

FIG. 9 shows the study design including dosing and sample collection schedule for the study in Example 5.

DETAILED DESCRIPTION

Figure 2B:
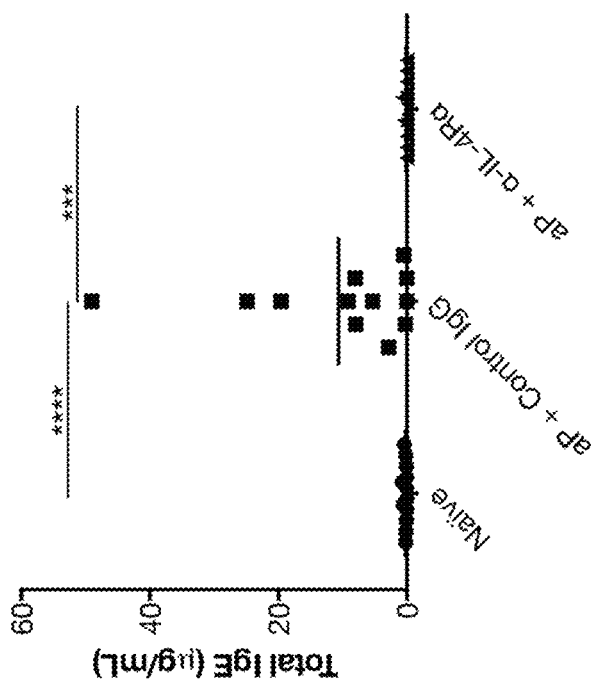
FIGS. 2A and 2B show serum total IgE levels in mice immunized with either TDaP, which includes the acellular pertussis (aP) vaccine (FIG. 2A) or with DTP, which includes the whole-cell pertussis (wP) vaccine (FIG. 2B) and treated with an isotype control antibody or with anti-mouse IL-4R antibody (anti-IL-4Rα). Results are the values for 4-12 mice per group. One-way ANOVA statistical analysis was performed: *$p<0.001$, **$p<0.0001$

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.). As used herein, the terms "treat", "treating", or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the present invention, the preferred methods and materials are now described. All publications mentioned herein are incorporated herein by reference to describe in their entirety.

General Description

Bacillus pertussis is a Gram-negative bacterium that causes pertussis (also called whooping cough), a highly contagious, severe and sometimes lethal respiratory infection in infants and children. Pertussis was largely controlled after introduction of whole cell pertussis (wP) vaccines (DTP or DPT) in 1943. wP vaccines typically comprise inactivated (heat-killed or chemically treated, usually by formalin) suspensions of the entire bacterial organism. However, wP vaccines were found to be associated with various adverse side effects including vaccine-induced fever, febrile seizures and central nervous system complications. Therefore, the wP vaccines were discontinued in the United States over such safety concerns and fully replaced in 1997 by acellular pertussis (aP) vaccines. aP vaccines contain inactivated pertussis toxin (PT) and one or more other bacterial components [i.e., filamentous hemagglutinin (FHA), pertactin (Pn), and fimbriae (Fim)] adsorbed to alum and have been widely used in the developed world since the 1990s. However, since the aP vaccines replaced the wP vaccines, pertussis has re-emerged as a public health concern. Reported pertussis cases among 7- to 10-year olds increased from 13% to 23% of reported cases with as many as 42,000 cases of pertussis reported in children in 2012 (Mills et al 2014; Trends Microbiol. 22: 49-52).

The mechanisms contributing to protective immunity have been studied for wP and aP vaccines in humans and in mouse models. The immune response observed with the wP vaccine closely resembles that of a naturally infected individual or challenged mouse. wP induces a T helper 1 (Th1)

response (i.e., an influx of neutrophils and production of IL-1, IL-12) (Redhead et al 1993, Infect. Immun. 61: 3190-8; Ross et al 2013, PLoS Pathog 9(4): e1003264.doi: 10.1371/journal.ppat.1003264). However wP also leads to formation of IgE and allergic reactions. On the other hand, the aP vaccine has a well-defined T helper 2 (Th2) response both in humans and in the preclinical mouse model wherein the Th2 response is induced via IL-4 production (Mills et al 1998, Infect. Immun. 66: 596-602). Subsequent studies have shown that Th2 response is not necessary for protective immunity in human and mouse models and that wP vaccines and previous infection are better than current aP vaccines in conferring protective immunity because they induce Th1 response (Ross et al 2013, PLoS Pathog 9(4): e1003264.doi: 10.1371/journal.ppat.1003264; Brummelman et al 2015, FEMS Pathog. Dis. doi: 10.1093/femspd/ftv067). aP vaccines fail to generate effective immunological memory leading to waning of protective immunity. In addition, the Th2 response elicited by aP vaccines leads to undesirable IgE and rare hypersensitivity reactions observed in children with $4^{th}$ or $5^{th}$ booster dose (Brummelman et al 2015, FEMS Pathog. Dis. doi: 10.1093/femspd/ftv067). Further, antigenic variation has been found in pertussis toxin, pertactin and fimbriae, leading to loss of protection against some currently circulating strains (Brummelman et al 2015, FEMS Pathog. Dis. doi: 10.1093/femspd/ftv067).

A new animal model of experimental pertussis in baboons uncovered a major deficit in protective immunity induced by aP vaccination (Warfel et al 2014, PNAS 111: 787). The study showed that animals with previous infection were not colonized after aerosolized challenge, whereas the wP vaccine prevented disease and enhanced bacterial clearance compared to naïve animals. In contrast, the aP vaccine produced a suboptimal immune response that prevented disease in vaccinated baboons but was unable to prevent infection or transmission to naïve baboons.

Various molecules have been studied as possible adjuvant candidates to increase the immunogenicity and duration of immunity afforded by aP vaccines, e.g., cytokines such as IL-1, IL-12 and GM-CSF, and Toll-like Receptor agonists (Dunne et al 2015, Mucosal Immunol. 8: 607-17; Allen & Mills 2014, Expert Rev. Vaccines 13: 1253-64). There is still an unmet need for improved vaccine compositions and vaccination strategies that prevent B. pertussis infection and transmission. The present inventors have shown herein that administration of an IL-4R antagonist (e.g., an anti-IL-4R antibody) with the aP vaccine results in the production of more Th1 type antigen-specific IgG isotype antibodies (e.g., IgG2a and b/c in mice, or IgG1 in humans) and reduction of IgE and Th2 type antigen-specific IgG isotype antibodies (e.g., IgG1 in mice, or IgG4 in humans), thus affording better protection in response to pathogen challenge. More generally, as shown herein the administration of an IL-4R antagonist (e.g., anti-IL-4R antibody) as an adjuvant in combination with a vaccine produces a Th1 response instead of a Th2 response, thus ensuring better efficacy of the vaccine and/or preventing adverse side effects of the vaccine (e.g., an allergic reaction).

Methods for Enhancing the Efficacy and/or Safety of Vaccines

The present invention includes methods which comprise administering to a subject in need thereof a vaccine in combination with a pharmaceutical composition comprising an IL-4R antagonist. The pharmaceutical composition comprising the IL-4R antagonist comprises a pharmaceutically accepted carrier or excipient. In certain embodiments, the IL-4R antagonist is administered before, after and/or concurrent with the vaccine.

As used herein, the expression "a subject in need thereof" means a human or a non-human animal that is susceptible to and/or is in need of preventive protection from a microbial (e.g., bacterial or viral) infection. In the context of the invention, the term "subject" includes a subject that is susceptible to an infection selected from the group consisting of pertussis, diphtheria, tetanus, tuberculosis, malaria, anthrax, cholera, typhoid, leprosy, Lyme's disease, streptococcal infection, E. coli infection, staphylococcal infection, plague, clostridial infection, meningococcal infection, pneumococcal infection, pneumonia, meningitis, sepsis, influenza, chickenpox, HIV infection, RSV infection, polio, small pox, rabies, rotavirus infection, papillomas, cervical cancer, Ebola, hepatitis, yellow fever, measles, mumps and Rubella infection.

In some embodiments, the term "subject" includes a child who is 3 years old. For example, the present methods may be used for infants who are less than 1 month, about 1 month, about 2 months, about 3 months, about 4 months, about 5 months, about 6 months, about 7 months, about 8 months, about 9 months, about 10 months, about 11 months or about 12 months old. In other embodiments, the methods of the present invention may be used to treat children who are about 1 year old, less than 1 year old, less than 2 years old, less than 3 years, less than 4 years, less than 5 years, less than 6 years, less than 7 years, less than 8 years, less than 9 years, less than 10 years, less than 11 years, less than 12 years, less than 13 years, less than 14 years, or less than 15 years old. In certain embodiments, the methods of the present invention may be used to treat adolescents who are about 15 years old, about 16 years old, about 17 years old, about 18 years old, about 19 years old, about 20 years old or less than 20 years old.

In certain embodiments, the term "subject" includes an adult more than 50 years old, more than 55 years old, more than 60 years old, more than 65 years old, more than 70 years old or more than 75 years old.

In certain embodiments, the term "subject" includes an adult more than 20 years old, more than 25 years old, more than 30 years old, more than 35 years old, more than 40 years old, more than 45 years old or more than 50 years old. In certain embodiments, the adult is not pre-immunized with a vaccine such as tetanus vaccine, diphtheria vaccine, or pertussis vaccine.

In certain embodiments, the term "subject" includes an adult or adolescent more than 10 years of age who has been immunized with a vaccine, but needs to get a booster dose of the vaccine. In certain embodiments, the term includes an adult who may have been pre-immunized but has developed compromised immunity to an infection and needs to receive an additional vaccine dose (e.g., a booster dose). In certain embodiments, the term "subject" includes subjects that are allergic to one or more components of a vaccine. In a further embodiment, the term includes subjects that may be at an increased risk of developing an allergic response to a vaccine.

In certain embodiments, the present invention provides methods to enhance efficacy and/or safety of a vaccine, the methods comprising administering one or more doses of said vaccine in combination with one or more doses of an IL-4R antagonist to a subject in need thereof.

In certain embodiments, the present invention provides methods to enhance or potentiate the immune response to a vaccine, the methods comprising administering one or more doses of said vaccine in combination with one or more doses of an IL-4R antagonist to a subject in need thereof.

As used herein, the term "to enhance the efficacy and/or safety of a vaccine" refers to increased protection and/or increased duration of protection afforded by administration of a vaccine in combination with an IL-4R antagonist to subsequent pathogen challenge, as compared to administration of the vaccine alone. In certain embodiments, the term includes one or more of the following: (a) prevention of disease due to a pathogenic bacterium or virus; (b) decreased bacterial or viral titers in the infected host or decreased pathogen load in infected host; (c) faster clearance of pathogen from infected host; (d) increased production of pathogen-specific Th1 type IgG isotype titers; (e) reduced or abrogated allergic response due to vaccine administration; (f) reduced or abrogated production of serum IgE in the host due to vaccine administration; (g) reduction in Th2 response; (h) decreased production of pathogen-specific Th2 type IgG isotype titers; (i) decrease in the number of vaccine doses required for protection; (j) prevention of infection and transmission of pathogen and/or infectious disease; and/or (k) long-lasting (durable) resistance to subsequent pathogen challenge, as compared to a subject administered with a vaccine alone. In certain embodiments, the term includes enhancing the safety of a vaccine. In certain embodiments, the term includes prevention or reduction or abrogation of one or more IgE-mediated responses to a vaccine, including, but not limited to urticaria, angioedema, anaphylaxis, gastro-intestinal disorders and discontinuation of booster dose(s) of vaccine leading to sub-optimal immune response to that vaccine. In one aspect, the present invention provides methods to produce an optimal immune response to a vaccine in a subject, the methods comprising administering an IL-4R antagonist in combination with a vaccine to the subject in need thereof.

According to one aspect, the present invention provides methods for preventing infection and/or transmission of an infectious disease to a subject. In certain embodiments, the present invention provides methods to increase herd immunity in a population that is susceptible to an infectious disease. The methods, according to this aspect, comprise administering an IL-4R antagonist in combination with a vaccine to a subject in need thereof.

In certain embodiments, the present invention provides methods to prevent, treat or reduce or ameliorate the severity of an adverse side effect elicited by administration of a vaccine in a subject in need thereof. Adverse side effects elicited by the vaccine include, but are not limited to, injection site reactions, allergic reactions, localized swelling, swelling of lymph nodes, and hypersensitivity. In certain particular embodiments, the present invention provides methods to prevent, treat or reduce or decrease the severity of an allergic response elicited by administration of a vaccine in a subject in need thereof. As used herein, the phrases "allergic response," "allergic reaction," "allergic symptom," and the like, include one or more signs or symptoms selected from the group consisting of urticaria (e.g., hives), angioedema, rhinitis, asthma, vomiting, sneezing, runny nose, sinus inflammation, watery eyes, wheezing, bronchospasm, reduced peak expiratory flow (PEF), gastro-intestinal distress, flushing, swollen lips, swollen tongue, reduced blood pressure, anaphylaxis, and organ dysfunction/failure. An "allergic response," "allergic reaction," "allergic symptom," etc., also includes immunological responses and reactions such as, e.g., an increased Th2 response, increased IgE production and/or increased allergen-specific immunoglobulin production. As used herein, the term "to decrease an allergic response" refers to absence or reduction in the severity of an allergic response.

In certain embodiments, the present invention includes methods to reduce serum total IgE levels induced by administration of a vaccine, the methods comprising administering one or more doses of the vaccine in combination with one or more doses of an IL-4R antagonist. As used herein, a reduction in serum IgE level means that the amount of IgE measured in the serum of a subject who has been administered a vaccine and who has been treated with an IL-4R antagonist, is at least 5%, 10%, 20%, 50%, 80%, or 90% lower than the serum IgE level measured in the same or an equivalent subject that has not been treated with the IL-4R antagonist. In certain embodiments, a reduction in serum IgE level means that no or negligible amounts of IgE are detected in the serum of a subject. As used herein, serum IgE may include total serum IgE and/or antigen-specific IgE (e.g., allergen-specific IgE).

In certain embodiments, the present invention provides methods to reduce Th2 response elicited upon administration of a vaccine in a subject in need thereof, the methods comprising administering one or more doses of the vaccine in combination with one or more doses of an IL-4R antagonist. In certain embodiments, reducing Th2 response includes, but is not limited to, reduction in serum IgE level that is elicited by the vaccine and/or decreased production of pathogen-specific Th2 type IgG isotype titers (e.g., IgG1 in mice, or IgG4 in humans).

The present invention includes methods for reducing susceptibility to an allergic response to a vaccine in a subject. As used herein, the term "subject" refers to subjects with increased susceptibility or at greater risk of developing an allergic response, e.g., subjects with atopic dermatitis. In this aspect, the term "subject" includes subjects with atopic dermatitis, greater allergen sensitization, and subjects with allergic rhinitis, asthma or food allergy. In certain embodiments, the present invention includes methods to reduce toxicity associated with vaccine administration in a patient with atopic dermatitis, the methods comprising administering one or more doses of an IL-4R antagonist in combination with said vaccine. The term "subject" also includes subjects with elevated levels of serum total and allergen-specific IgE, or serum chemokines (e.g., CCL17 or CCL27).

According to certain aspects, the present invention provides methods to increase duration of immunity induced by a vaccine in a subject in need thereof. It is known in the art that some vaccines, e.g., acellular pertussis vaccine, show shorter duration of protection, thus necessitating regular booster doses in subjects such as older children, adolescents, adults or the elderly. These booster doses result in undesirable hypersensitivity reactions in subjects. Accordingly, in certain embodiments, the present invention provides methods to reduce the number of booster doses needed for providing protection against pathogen challenge in a subject. The methods, according to this aspect, comprise administering a vaccine in combination with a pharmaceutical composition comprising an IL-4R antagonist. The methods, as disclosed herein, lead to similar or better immune protection against pathogen challenge even with reduced doses of the vaccine. In certain embodiments, the invention provides for methods to reduce the number of vaccine doses by one or more doses, e.g., by one dose, by two doses, by three doses or more, as compared to a subject not administered an IL-4R antagonist. In particular embodiments, the administration of one dose of a vaccine in combination with one or more doses of an IL-4R antagonist is at least as efficacious as 2 doses of vaccine without IL-4R antagonist. In another embodiment, administration of one or two doses of vaccine in combination with one or more doses of an IL-4R antagonist is at least as efficacious as three doses of vaccine without IL-4R antagonist.

The methods of the present invention, according to certain embodiments, comprise administering to the subject a vaccine in combination with an IL-4R antagonist. As used herein, the expression "in combination with" means that the vaccine is administered before, after, or concurrent with the pharmaceutical composition comprising the IL-4R antagonist. The term "in combination with" also includes sequential or concomitant administration of IL-4R antagonist and a vaccine.

For example, when administered "before" administration of the vaccine, the IL-4R antagonist may be administered about 10 weeks, about 9 weeks, about 8 weeks, about 7 weeks, about 6 weeks, about 5 weeks, about 4 weeks, about 3 weeks, about 2 weeks, or about 1 week prior to the administration of the vaccine. In certain embodiments, the IL-4R antagonist may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the vaccine. When administered "after" the vaccine, the pharmaceutical composition comprising the IL-4R antagonist may be administered about 1 week, about 2 weeks, about 3 weeks, about 4 weeks, about 5 weeks, about 6 weeks, about 7 weeks, about 8 weeks, about 9 weeks or about 10 weeks after administration of the vaccine. In certain embodiments, the IL-4R antagonist may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the vaccine. Administration "concurrent" or "concomitant" with the vaccine means that the IL-4R antagonist is administered to the subject in a separate dosage form within less than 10 minutes (before, after, or at the same time) of administration of the vaccine, or administered to the subject as a single combined dosage formulation comprising both the vaccine and the IL-4R antagonist.

The present invention includes methods for increasing the efficacy and/or safety of a vaccine comprising administering said vaccine in combination with an effective amount of a pharmaceutical composition comprising an IL-4R antagonist to a subject in need thereof, wherein the pharmaceutical composition is administered to the subject in multiple doses, e.g., as part of a specific vaccination dosing regimen. For example, the vaccination dosing regimen may comprise administering multiple doses of the pharmaceutical composition to the subject at a frequency of about once a day, once every two days, once every three days, once every four days, once every five days, once every six days, once a week, once every two weeks, once every three weeks, once every four weeks, once a month, once every two months, once every three months, once every four months, or less frequently, followed by one or more doses of the vaccine.

In certain embodiments, each dose of the IL-4R antagonist comprises 1-50 mg/kg of the subject's body weight. In certain embodiments, each dose of the IL-4R antagonist comprises 10-600 mg of the IL-4R antagonist.

In related aspects, the present invention provides vaccination regimens in a subject comprising administration of one or more doses of an IL-4R antagonist followed by a dose of the IL-4R antagonist concurrent with a vaccine, optionally followed by one or more doses of the IL-4R antagonist. In certain embodiments, the vaccination regimen comprises administration of 1-10 weekly doses of an IL-4R antagonist followed by a dose of IL-4R antagonist concurrent with a vaccine followed by 1-3 weekly doses of the IL-4R antagonist. In certain embodiments, the vaccination regimen comprises one or more booster doses of the vaccine. In further embodiments, each booster dose of the vaccine is administered following one or more doses of an IL-4R antagonist.

Methods for Treating Atopic Dermatitis

According to certain aspects, the present invention provides methods for treating atopic dermatitis (AD) in a patient without interfering with the patient's response to a vaccine. In certain embodiments, the present invention provides methods for treating AD in a patient without suppressing the patient's response to a vaccine. In certain embodiments, the present invention provides methods for treating AD in a patient wherein the patient is susceptible to a microbial infection and/or wherein the patient is in need of a vaccine against an infectious disease. The methods, according to these aspects, comprise administering to a subject in need thereof a therapeutic composition comprising an IL-4R antagonist. In certain embodiments, the methods comprise selecting a patient diagnosed with atopic dermatitis who has recently been or will be inoculated with a vaccine and administering to the patient one or more doses of an IL-4R antagonist, wherein the IL-4R antagonist does not reduce or attenuate the patient's response to the vaccine. As used herein, the term "patient's response to a vaccine" refers to the protective immune response to a vaccine in a patient. In the context of the present invention, the term refers to the level of antibodies produced in patients with AD treated or not with dupilumab. As used herein, the expression "a patient in need thereof" means a human animal that exhibits one or more symptoms or indicia of atopic dermatitis, and/or who has been diagnosed with atopic dermatitis. In certain embodiments, the methods of the present invention may be used to treat patients that show elevated levels of one or more AD-associated biomarkers (e.g., IgE). AD-associated biomarkers are described in US Patent Publication No. US20140072583, incorporated herein in its entirety. For example, the methods of the present invention comprise administering an IL-4R antagonist to patients with elevated levels of IgE or TARC or periostin. In the context of the present invention, "a patient in need thereof" may include, e.g., patients who, prior to treatment, exhibit (or have exhibited) one or more AD-associated parameters such as, e.g., elevated IGA, BSA, EASI, SCORAD, 5D-Pruritus, and/or NRS score, and/or an elevated level of one or more AD-associated biomarker such as, e.g., IgE and/or TARC. In certain embodiments, "a subject in need thereof" may include a subset of population which is more susceptible to AD or may show an elevated level of an AD-associated biomarker. For example, "a subject in need thereof" may include a subset of population defined by a race or an ethnicity present in the population.

In some embodiments, the methods herein may be used to treat AD in children who are 1 year old. For example, the present methods may be used to treat infants who are less than 1 month, 1 month, 2 months, 3 months, 4 months, 5 months, 6 months, 7 months, 8 months, 9 months, 10 months, 11 months or less than 12 months old. In other embodiments, the present methods may be used to treat children and/or adolescents who are 18 years old. For example, the present methods may be used to treat children or adolescents less than 17 years, 16 years, 15 years, 14 years, 13 years, 12 years, 11 years, 10 years, 9 years, 8 years, 7 years, 6 years, 5 years, 4 years, 3 years, or less than 2 years old. In specific embodiments, the present methods may be used to treat AD in children who are in need of a vaccine against an infectious disease (e.g., pertussis, diphtheria, tuberculosis, RSV, measles, mumps, and Rubella).

In certain embodiments, the patient in need thereof is an adult with AD and more than 20 years of age that might need a booster dose of a vaccine.

"Atopic dermatitis" (AD), as used herein, means an inflammatory skin disease characterized by intense pruritus (e.g., severe itch) and by scaly and dry eczematous lesions. The term "atopic dermatitis" includes, but is not limited to, AD caused by or associated with epidermal barrier dysfunction, allergy (e.g., allergy to certain foods, pollen, mold, dust mite, animals, etc.), radiation exposure, and/or asthma. The present invention encompasses methods to treat patients with mild, moderate-to-severe or severe AD. As used herein, "moderate-to-severe AD", is characterized by intensely pruritic, widespread skin lesions that are often complicated by persistent bacterial, viral or fungal infections. Moderate-to-severe AD also includes chronic AD in patients. In many cases, the chronic lesions include thickened plaques of skin, lichenification and fibrous papules. Patients affected by moderate-to-severe AD also, in general, have more than 20% of the body's skin affected, or 10% of skin area in addition to involvement of the eyes, hands and body folds. Moderate-to-severe AD is also considered to be present in patients who require frequent treatment with topical corticosteroids. A patient may also be said to have moderate-to-severe AD when the patient is resistant or refractory to treatment by either a topical corticosteroid or a calcineurin inhibitor or any other commonly used therapeutic agent known in the art. A patient with moderate-to-severe or severe AD also may show more exacerbations or flares of the disease.

The present invention includes methods to treat AD in patients resistant, non-responsive or inadequately responsive to treatment with a topical corticosteroid (TCS) or a calcineurin inhibitor. The term "resistant, non-responsive or inadequately responsive to a TCS or a calcineurin inhibitor", as used herein, refers to subjects or patients with AD who have been treated with a TCS or a calcineurin inhibitor and wherein the TCS/calcineurin inhibitor does not have a therapeutic effect. In some embodiments, the term refers to reduced patient compliance and/or toxicity and side effects and/or ineffectiveness of the administered TCS/calcineurin inhibitor to reduce, ameliorate or decrease the symptoms of AD. In some embodiments, the term refers to patients suffering from moderate-to-severe AD who are refractory to treatment by a TCS/calcineurin inhibitor. In some embodiments, the term refers to patients with AD which is uncontrolled despite treatment with a TCS and/or calcineurin inhibitor. In some embodiments, the patients who are "resistant, non-responsive or inadequately responsive to a TCS or a calcineurin inhibitor" may show no improvement in one or more AD-associated parameters. Examples of AD-associated parameters are described elsewhere herein. For example, treatment with a TCS/calcineurin inhibitor may result in no decrease in pruritus or EASI score or BSA score. In some embodiments, the present invention includes methods to treat moderate-to-severe AD in patients who have been treated earlier with a TCS/calcineurin inhibitor for ≥1 month and do not show a decrease in one or more AD-associated parameters. For example, the present methods may be used to treat a patient with chronic AD who has been on a stable regimen of a TCS/calcineurin inhibitor and has a BSA score of ≥10% or an IGA score ≥3.

In certain embodiments, the present invention provides methods wherein administration of an IL-4R antagonist results in improvement in one or more AD-associated parameters. Examples of "AD-associated parameters" include: (a) Investigators Global Assessment (IGA); (b) Body Surface Area Involvement of Atopic Dermatitis (BSA); (c) Eczema Area and Severity Index (EASI); (d) SCORAD; (e) 5-D Pruritus Scale; and (f) Pruritus Numeric Rating Scale (NRS). AD-associated parameters are described in US Patent Publication No. US20140072583, incorporated herein in its entirety. An "improvement in an AD-associated parameter" means a decrease from baseline of one or more of IGA, BSA, EASI, SCORAD, 5-D Pruritus Scale, or NRS. As used herein, the term "baseline," with regard to an AD-associated parameter, means the numerical value of the AD-associated parameter for a subject prior to or at the time of administration of a pharmaceutical composition of the present invention.

To determine whether an AD-associated parameter has "improved," the parameter is quantified at baseline and at one or more time points after administration of the pharmaceutical composition of the present invention. For example, an AD-associated parameter may be measured at day 1, day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present invention. The difference between the value of the parameter at a particular time point following initiation of treatment and the value of the parameter at baseline is used to establish whether there has been an "improvement" (e.g., a decrease) in the AD associated parameter.

Interleukin-4 Receptor Antagonists

The methods of the present invention comprise administering to a subject in need thereof a therapeutic composition comprising an interleukin-4 receptor (IL-4R) antagonist. As used herein, an "IL-4R antagonist" (also referred to herein as an "IL-4R inhibitor," an "IL-4Rα antagonist," an "IL-4R blocker," an "IL-4Rα blocker," etc.) is any agent which binds to or interacts with IL-4Rα or an IL-4R ligand, and inhibits or attenuates the normal biological signaling function a type 1 and/or a type 2 IL-4 receptor. Human IL-4Rα has the amino acid sequence of SEQ ID NO: 13. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R antagonists that can be used in the methods of the present invention may function by blocking IL-4-mediated signaling, IL-13-mediated signaling, or both IL-4- and IL-13-mediated signaling. The IL-4R antagonists of the present invention may thus prevent the interaction of IL-4 and/or IL-13 with a type 1 or type 2 receptor.

Non-limiting examples of categories of IL-4R antagonists include small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R antagonists also include antigen-binding proteins that specifically bind IL-4 and/or IL-13.

Anti-IL-4Rα Antibodies and Antigen-Binding Fragments Thereof

According to certain exemplary embodiments of the present invention, the IL-4R antagonist is an anti-IL-4Rα antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$, (v) $V_H$-$C_H1$-$C_H2$-$C_H3$; $V_H$-$C_H2$-$C_H3$; $V_H$-$C_L$; $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab[2] bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present invention specifically bind IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα, as used in the context of the present invention, includes antibodies that bind IL-4Rα or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 1 nM, less than about 0.5 nM, less than about 0.25 nM, less than about 0.1 nM or less than about 0.05 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present invention, the IL-4R antagonist is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In some embodiments, the anti-IL-4R antibody or antigen-binding fragment thereof comprises an HCVR comprising SEQ ID NO: 1 and an LCVR comprising SEQ ID NO: 2. According to certain exemplary embodiments, the methods of the present invention comprise the use of the anti-IL-4R antibody comprising HCDR1-HCDR2-HCDR3-LCDR1-LCDR2-LCDR3 amino acid sequences of SEQ ID NOs: 3-4-5-6-7-8 (referred to and known in the art as "dupilumab"), or a bioequivalent thereof. In certain embodiments, the methods of the present invention comprise the use of an anti-IL-4R antibody, wherein the antibody comprises a heavy chain comprising the amino acid sequence of SEQ ID NO: 9. In some embodiments, the anti-IL-4R antibody comprises a light chain comprising the amino acid sequence of SEQ ID NO: 10. An exemplary antibody comprising a heavy chain comprising the amino acid sequence of SEQ ID NO: 9 and a light chain comprising the amino acid sequence of SEQ ID NO: 10 is the fully human anti-IL-4R antibody known as dupilumab. According to certain exemplary embodiments, the methods of the present invention comprise the use of dupilumab, or a bioequivalent thereof. The term "bioequivalent", as used herein, refers to anti-IL-4R antibodies or IL-4R-binding proteins or fragments thereof that are pharmaceutical equivalents or pharmaceutical alternatives whose rate and/or extent of absorption do not show a significant difference with that of dupilumab when administered at the same molar dose under similar experimental conditions, either single dose or multiple dose. In the context of the invention, the term refers to antigen-binding proteins that bind to IL-4R which do not have clinically meaningful differences with dupilumab in their safety, purity and/or potency.

In certain particular embodiments, the methods of the present invention comprise the use of an anti-mouse anti-IL-4R antibody or antigen-binding fragment thereof comprising an HCVR sequence of SEQ ID NO: 11 and an LCVR sequence of SEQ ID NO: 12. In an exemplary embodiment, the methods of the present invention comprise the use of an anti-mouse anti-IL-4R antibody in increasing the efficacy and/or safety of a pertussis vaccine in a *Bordetella pertussis* aerosol challenge mouse model.

In certain particular embodiments, the methods of the present invention comprise the use of an anti-monkey anti-IL-4R antibody or antigen-binding fragment thereof comprising an HCVR sequence of SEQ ID NO: 14 and an LCVR sequence of SEQ ID NO: 15. In an exemplary embodiment, the methods of the present invention comprise the use of an anti-monkey anti-IL-4R antibody in increasing the efficacy and/or safety of a pertussis vaccine in the clinically relevant infant baboon model.

Other anti-IL-4Rα antibodies that can be used in the context of the methods of the present invention include, e.g., the antibody referred to and known in the art as AMG317 (Corren et al., 2010, *Am J Respir Crit Care Med.*, 181(8): 788-796), or any of the anti-IL-4Rα antibodies as set forth in U.S. Pat. Nos. 7,186,809, 7,605,237, 7,608,693, or 8,092,804.

The anti-IL-4Rα antibodies used in the context of the methods of the present invention may have pH-dependent binding characteristics. For example, an anti-IL-4Rα antibody for use in the methods of the present invention may exhibit reduced binding to IL-4Rα at acidic pH as compared to neutral pH. Alternatively, an anti-IL-4Rα antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Pharmaceutical Compositions

The present invention includes methods which comprise administering an IL-4R antagonist to a patient, wherein the IL-4R antagonist is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient according to the methods of the present invention may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351). Specific exemplary doses of anti-IL4R antibodies and administration regimens involving the same that can be used in the context of the present invention are disclosed elsewhere herein.

Various delivery systems are known and can be used to administer the pharmaceutical composition comprising an IL-4R antagonist, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PROT™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present invention are disclosed, e.g., in U.S. Pat. No. 8,945,559.

Vaccine Compositions

In certain embodiments, the present invention provides a vaccine composition comprising a vaccine adjuvant, wherein the vaccine adjuvant comprises an IL-4R antagonist. As used herein, the term "adjuvant" refers to any substance that acts to accelerate, prolong, or enhance antigen-specific immune responses when used in combination with specific vaccine antigens. In the context of the invention, the adjuvant (e.g., an IL-4R antagonist) has the property of increasing the efficacy of a vaccine in a subject, as compared to a subject that is administered the vaccine without the IL-4R antagonist. In certain embodiments, the use of the IL-4R antagonist increases the safety of the administered vaccine, for example, by decreasing the risk of an allergic reaction to a vaccine component. In certain embodiments, the use of the IL-4R antagonist as adjuvant enables to decrease the number of administered doses of the vaccine. For example, an administration of one dose of vaccine composition with the adjuvant (i.e., an IL-4R antagonist) according to the invention is as efficient as the administration of two doses of vaccine without the adjuvant according to the invention. Similarly, an administration of one or two doses of vaccine according to the invention with the adjuvant according to the invention is as efficient as the administration of three doses of vaccine without the adjuvant according to the invention. In certain embodiments, the vaccine composition comprises a second adjuvant (e.g., alum).

In certain embodiments, the IL-4R antagonist is an anti-IL-4R antibody or antigen-binding fragment thereof, as described herein. In certain exemplary embodiments, the anti-IL-4R antibody or antigen-binding fragment thereof comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. In certain embodiments, the anti-IL-4R antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

The immunogen or antigen suitable for use in the vaccine compositions of the present invention may be selected from the group consisting of inactivated pathogens, attenuated pathogens, immunogenic sub-units (e.g. proteins, polypeptides, peptides, epitopes, haptens), or recombinant expression vectors, including plasmids having immunogenic inserts. In one embodiment of the present invention, the immunogen is an inactivated or killed microorganism. In certain embodiments, the vaccine composition comprises a component from a microbial organism selected from the group consisting of *Bordetella pertussis, Corynebacterium diptheriae, Clostridium tetani, Mycobacterium tuberculosis, Plasmodium* spp., *Bacillus anthracis, Vibrio cholera, Salmonella typhi, Borrelia* spp., *Streptococus pneumoniae, Staphylococcus aureus, Escherichia coli, Clostridium* spp., *Mycobacterium leprae, Yersinia pestis*, influenza virus, varicella zoster virus, human immunodeficiency virus (HIV), respiratory syncytial virus (RSV), polio virus, variola virus, rabies virus, rotavirus, human papillomavirus, Ebola virus, hepatitis A virus, hepatitis B virus, hepatitis C virus, lyssavirus, measles virus, mumps virus, and Rubella virus. In certain embodiments, the vaccine composition comprises a vaccine component selected from the group consisting of tetanus toxoid, diphtheria toxoid, inactivated pertussis toxin, filamentous hemagglutinin, pertactin, fimbriae type 2, fimbriae type 3, and formalin-inactivated respiratory syncytial virus.

The vaccine compositions of the present invention comprise at least one pharmaceutically acceptable carrier. The term "pharmaceutically acceptable carrier" refers to a carrier that may be administered to a patient, together with an antigen, and does not destroy the pharmacological activity thereof and is non-toxic when administered in doses sufficient to deliver a pharmaceutically effective amount of the compound. The pharmaceutically acceptable vehicles or excipients of use are conventional. Remington's Pharmaceutical Sciences, by E. W. Martin, Mack Publishing Co., Easton, Pa., 15th Edition (1975), describes compositions and formulations suitable for pharmaceutical delivery of a vaccine. In general, the nature of the vehicle or excipient will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, freeze-dried pastille, powder, pill, tablet, or capsule forms), conventional non-toxic solid vehicles or excipients can include, for example, pharmaceutical grades of mannitol, lactose, starch, or magnesium stearate. In addition to biologically neutral vehicles or excipients, immunogenic compositions to be administered can contain minor amounts of non-toxic auxiliary substances, such as wetting or emulsifying agents, preservatives, and pH buffering agents and the like, for example sodium acetate or sorbitan monolaurate.

As will be appreciated by persons skilled in the art, vaccines are suitably formulated to be compatible with the intended route of administration. Examples of suitable routes of administration include parenteral, e.g., intravenous, intradermal, subcutaneous, intramuscular, intraperitoneal, oral (e.g., buccal, inhalation, nasal and pulmonary spray), intradermal, transdermal (topical), transmucosal, and intraocular administration.

Administration Regimens

The methods of the present invention, according to certain embodiments, comprise administering to the subject a vaccine in combination with an IL-4R antagonist (e.g., an anti-IL-4R antibody). As used herein, the expression "in combination with" means that the vaccine is administered before, after, or concurrent with the IL-4R antagonist. The term "in combination with" also includes sequential or concomitant administration of IL-4R antagonist and a vaccine.

For example, when administered "before" the IL-4R antagonist, the vaccine may be administered more than 72 hours, about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the IL-4R antagonist. When administered "after" the IL-4R antagonist, the vaccine may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the IL-4R antagonist. Administration "concurrent" with the IL-4R antagonist means that the vaccine is administered to the subject in a separate dosage form within less than 5 minutes (before, after, or at the same time) of administration of the IL-4R antagonist, or administered to the subject as a single combined dosage formulation comprising both the vaccine and the IL-4R antagonist.

The present invention includes methods comprising administering to a subject an IL-4R antagonist at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of an anti-IL-4R antibody, once a week dosing at an amount of about 25 mg, 50 mg, 150 mg, or 300 mg, can be employed.

According to certain embodiments of the present invention, multiple doses of an IL-4R antagonist may be administered to a subject over a defined time course. The methods according to this aspect of the invention comprise sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks or months). The present invention includes methods which comprise sequentially administering to the patient a single initial dose of an IL-4R antagonist, followed by one or more secondary doses of the IL-4R antagonist, and optionally followed by one or more tertiary doses of the IL-4R antagonist.

The terms "initial dose," "secondary doses," and "tertiary doses," refer to the temporal sequence of administration of the IL-4R antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-4R antagonist, but generally may differ from one another in terms of frequency of administration. In certain embodiments, however, the amount of IL-4R antagonist contained in the initial, secondary and/or tertiary doses varies from one another (e.g., adjusted up or down as appropriate) during the course of treatment. In certain embodiments, the initial dose comprises a first amount of the antibody or antigen-binding fragment thereof and the one or more secondary doses each comprise a second amount of the antibody or antigen-binding fragment thereof. In some embodiments, the first amount of antibody or fragment thereof is 1.5×, 2×, 2.5×, 3×, 3.5×, 4×, or 5× the second amount of the antibody or antigen-binding fragment thereof. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4R antagonist may be administered to a patient in need thereof at a loading dose of about 300 mg to about 600 mg followed by one or more maintenance doses of about 25 mg to about 300 mg. In one embodiment, the initial dose and the one or more secondary doses each include 10 mg to 600 mg of the IL-4R antagonist, e.g., 100 mg to 400 mg of the IL-4R antagonist, e.g., 10 mg, 25 mg, 50 mg, 100 mg, 150 mg, 200 mg, 250 mg, 300 mg, 400 mg or 500 mg of the IL-4R antagonist.

In one exemplary embodiment of the present invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R antagonist which is administered to a patient prior to the administration of the very next dose in the sequence with no intervening doses.

The methods according to this aspect of the invention may comprise administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 6 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the regimen.

Dosage

The amount of IL-4R antagonist (e.g., anti-IL-4R antibody) administered in combination with a vaccine to a subject according to the methods of the present invention is, generally, an immunologically effective amount. As used herein, the phrase "immunologically effective amount" means an amount of IL-4R antagonist that leads to increase in the efficacy of a vaccine, or enhanced or increased immune response to a vaccine. In the context of the invention, the phrase "immunologically effective amount" means an amount of IL-4R antagonist that results in one or more of: (a) faster clearance of microbial pathogen from the infected host; (b) reduction in IgE level elicited by a vaccine; (c) an increase in Th1-type antigen-specific IgG; (d) reduction in Th2-type antigen-specific IgG levels; (e) reduction in the number of vaccine doses; and/or (f) better protection against and delay of infection upon pathogen challenge. In certain embodiments, the term "immunologically effective amount" includes prophylactically effective amount or a therapeutically effective amount of IL-4R antagonist, which means an amount needed for an effective immune response to prevent or treat or ameliorate a symptom or indication of an infectious disease. In certain embodiments, the phrase "immunologically effective amount" means an amount of IL-4R antagonist that results in a detectable improvement in one or more symptoms or indicia in a patient with atopic dermatitis, asthma, nasal polyposis, chronic rhinosinusitis, eosinophilic esophagitis, or allergy.

In the case of an anti-IL-4R antibody, an immunologically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 10 mg, 25 mg, 50 mg, 75 mg, 150 mg, or 300 mg of an anti-IL-4R antibody is administered to a subject.

The amount of IL-4R antagonist contained within the individual doses may be expressed in terms of milligrams of antibody per kilogram of subject body weight (i.e., mg/kg). For example, the IL-4R antagonist may be administered to a subject at a dose of about 0.0001 to about 100 mg/kg of subject body weight.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Administration of an Anti-IL-4R Antibody Significantly Reduces Serum Total IgE Induced by Pertussis Vaccine In this Example, the effect of an anti-IL-4R antibody on total serum IgE levels induced by a whole cell pertussis (wP) or acellular pertussis (aP) vaccine was assessed using the *Bordetella pertussis* aerosol challenge infection model. It is known in the art that tetanus as well as wP and aP vaccines induce log-scale boosting of IgE in some patients. Table 1 lists the components of aP and wP vaccines used in the Examples herein.

TABLE 1

Components of acellular pertussis (aP; TDaP) and whole-cell pertussis (wP; DTP) vaccines

| Vaccine component | TDaP Adacel (sanofi pasteur) | DTP Triple Antigen (Serum Institute of India) |
|---|---|---|
| Tetanus toxoid | 5 Lf | ≥5 Lf |
| Diptheria toxoid | 2 Lf | ≤25 Lf |
| Whole-cell *Bordetella pertussis* | — | ≥4 IU |
| Inactivated pertussis toxin | 2.5 µg | — |
| Filamentous hemagglutinin | 5 µg | — |
| Pertactin | 3 µg | — |
| Fimbriae types 2 and 3 | 5 µg | — |

TABLE 1-continued

Components of acellular pertussis (aP; TDaP)
and whole-cell pertussis (wP; DTP) vaccines

| Vaccine component | TDaP Adacel (sanofi pasteur) | DTP Triple Antigen (Serum Institute of India) |
|---|---|---|
| Aluminum (from aluminum phosphate) | 1.5 mg | ≥1.5 mg |

IU: international units;
Lf: limit of flocculation units

Figure 1:
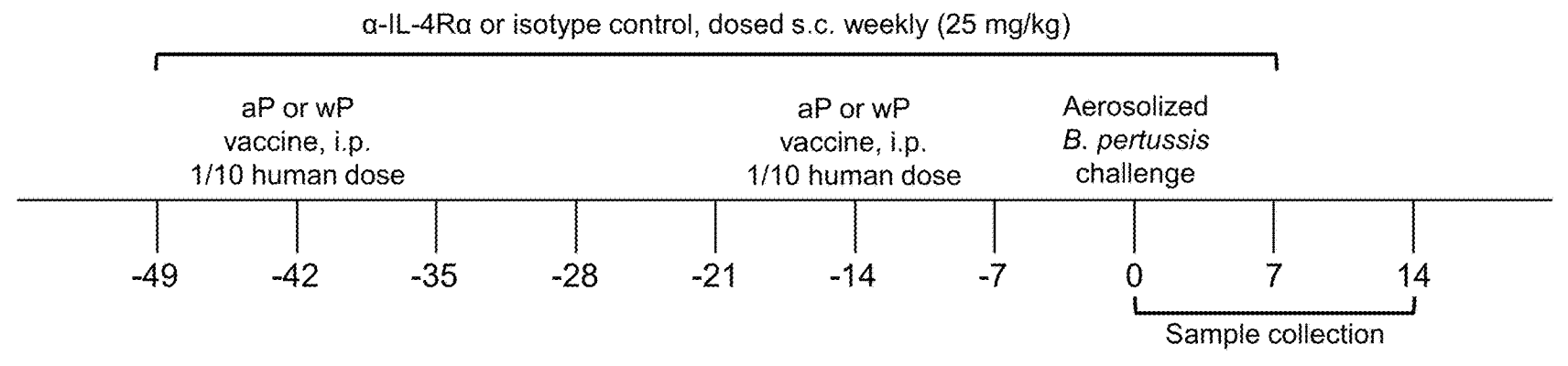

C57BL/6 mice were immunized with either TDaP [Adacel® (Sanofi Pasteur)] or DTP vaccine (Serum Institute of India, Pune, India) on Days −42 and −14 before an aerosol challenge with a virulent strain of *B. pertussis* (Day 0). Treatments with an anti-mouse IL-4R antibody ("anti-IL-4Rα") or isotype control antibody commenced one week before initial immunization and continued weekly up to Day 7. The treatment regime is outlined in FIG. 1. The anti-IL-4Rα antibody used in this Example was an anti-mouse-IL-4R antibody comprising an HCVR with an amino acid sequence of SEQ ID NO: 11 and an LCVR with an amino acid sequence comprising SEQ ID NO: 12.

Serum was collected from naive and immunized mice (12 mice per group) on the day 0. Total IgE levels were analyzed by ELISA. Total serum IgE levels were determined by ELISA using biotin-conjugated anti-mouse IgE antibody and peroxidase-conjugated streptavidin. Antibody levels are expressed as total IgE (μg/mL) as determined from a standard curve.

Figure 2A:
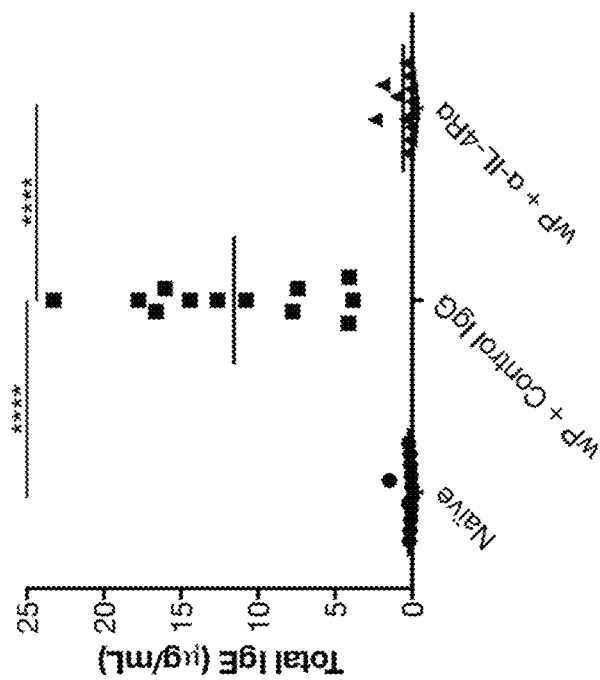
Figure 3A:
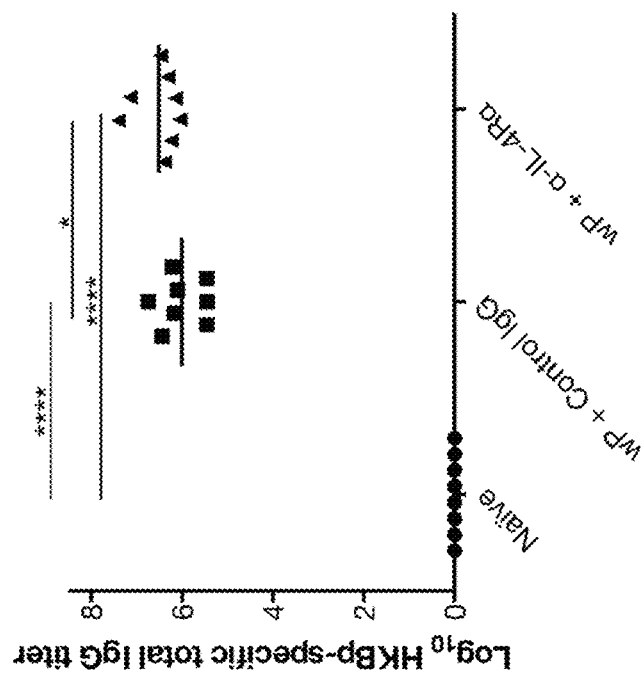
FIGS. 3A and 3B show (FIG. 3A) filamentous hemagglutinin (FHA)-specific total IgG titers in aP-immunized and (FIG. 3B) heat-killed Bordetella pertussis (HKBp)-specific total IgG titers in wP-immunized mice. Results are the values for 4-12 mice per group. *$p<0.05$, **$p<0.0001$
Figure 3B:
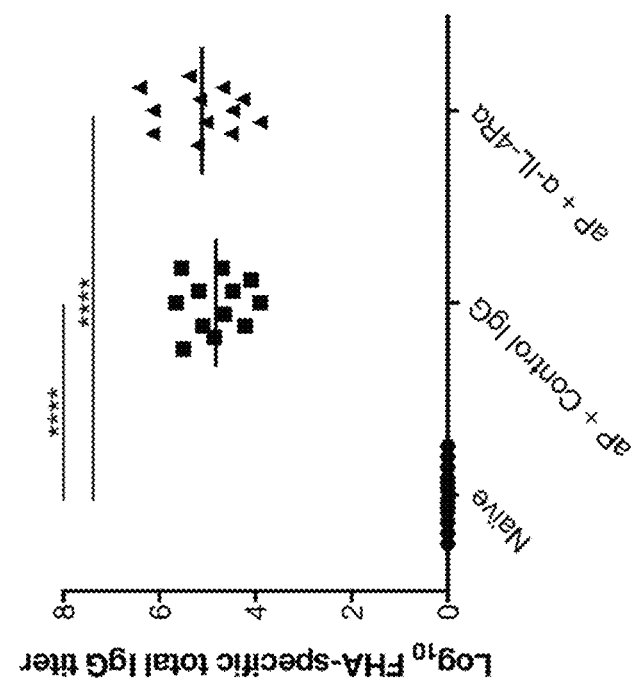
Figure 4B:
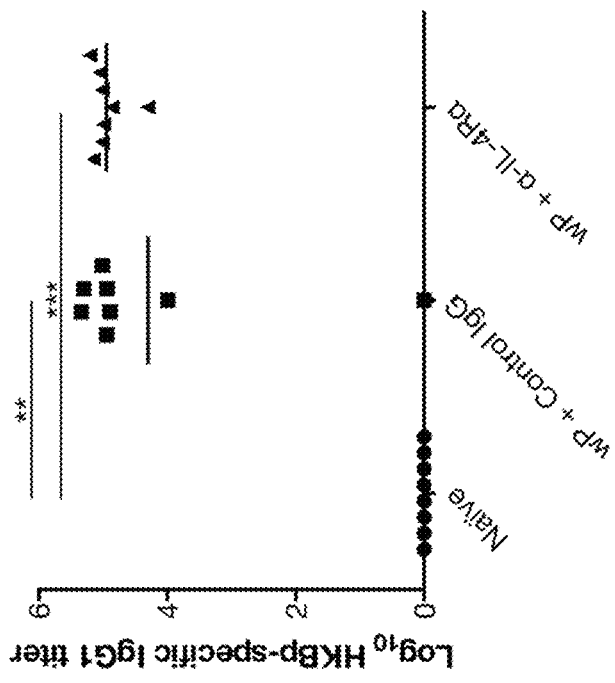
FIGS. 4A and 4B show (FIG. 4A) FHA-specific IgG1 titers in aP-immunized and (FIG. 4B) HKBp-specific IgG1 titers in wP-immunized mice. Results are the values for 4-12 mice per group. One-way ANOVA statistical analysis was performed. $p<0.01$, *$p<0.001$, $p<0.0001$
Figure 4A:
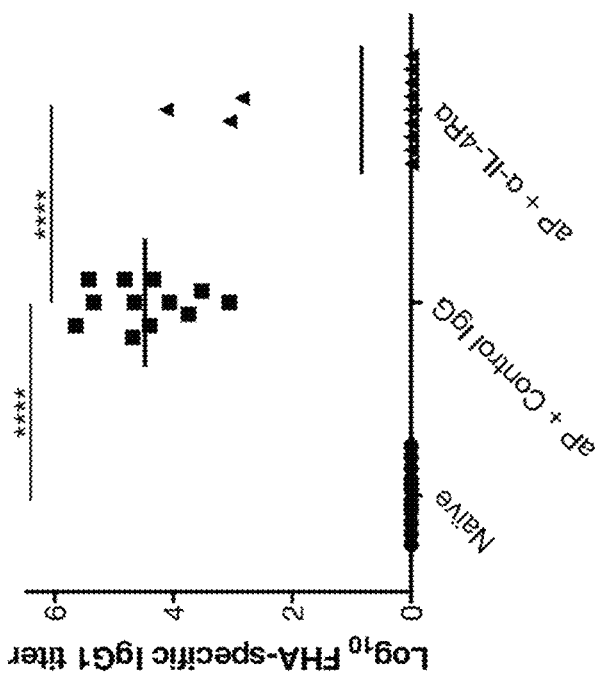
Figure 5A:
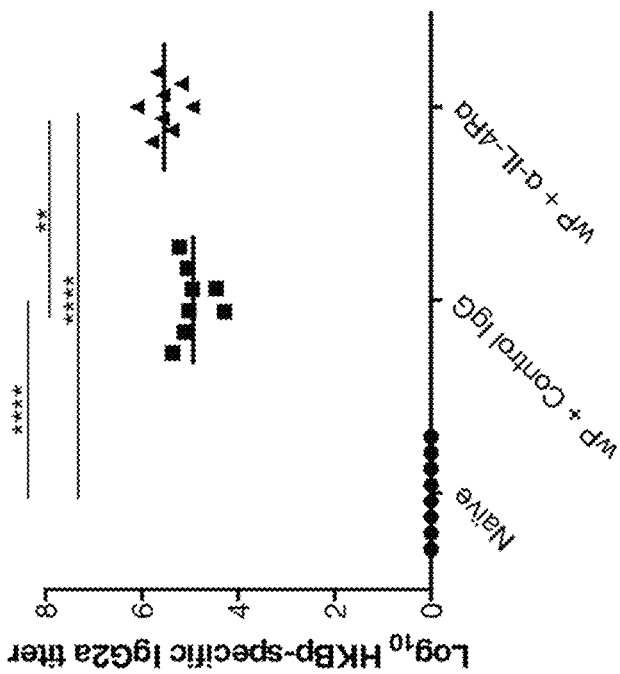
FIGS. 5A and 5B show (FIG. 5A) FHA-specific IgG2a titers in aP-immunized and (FIG. 5B) HKBp-specific IgG2a titers in wP-immunized mice. Results are the mean values for 4-12 mice per group. One-way ANOVA statistical analysis was performed. $p<0.01$, *$p<0.001$, **$p<0.0001$
Figure 5B:
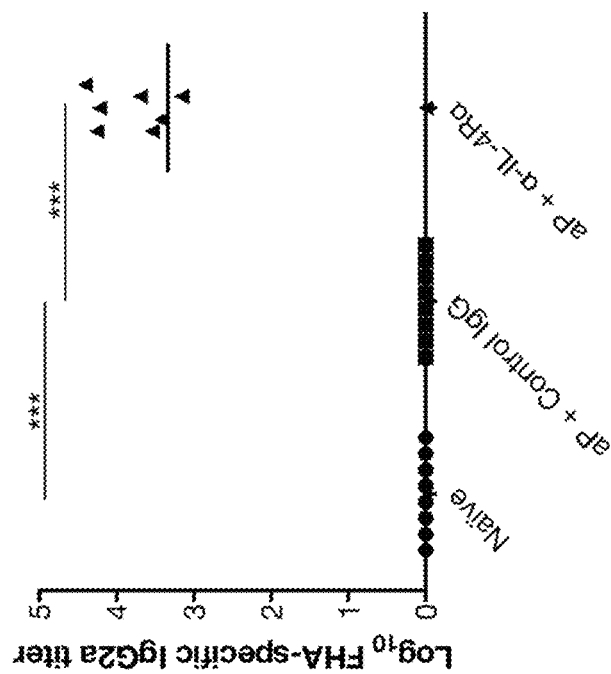
Figure 6A:
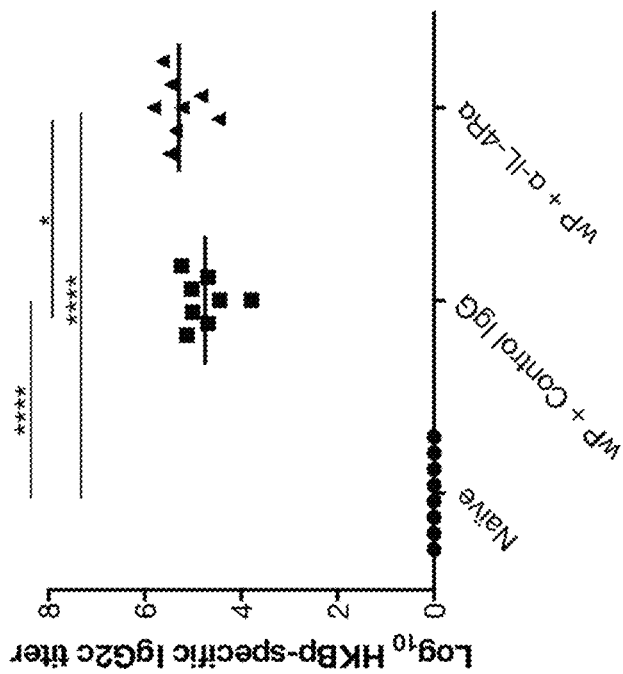
FIGS. 6A and 6B show (FIG. 6A) FHA-specific IgG2c titers in aP-immunized and (FIG. 6B) HKBp-specific IgG2c titers in wP-immunized mice. Results are the values for 4-12 mice per group. One-way ANOVA statistical analysis was performed. *$p<0.05$, **$p<0.0001$
Figure 6B:
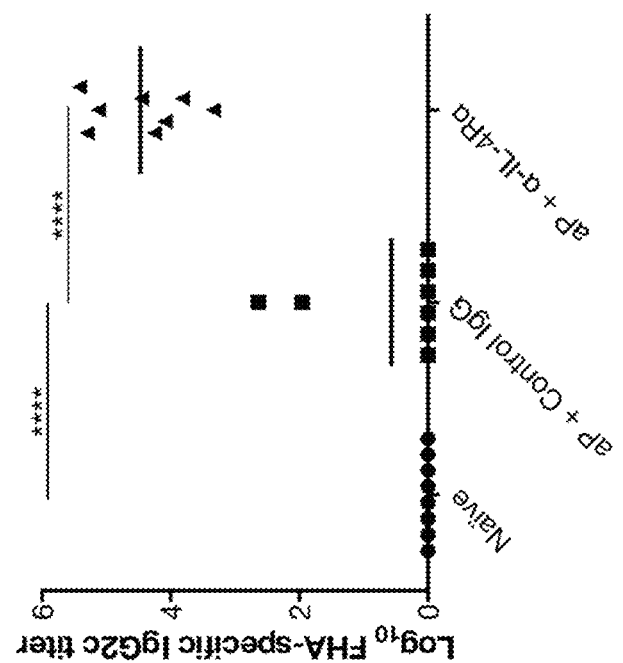

Treatment of mice with anti-IL-4Rα significantly decreased total serum IgE levels in mice that were immunized with TDaP (aP) and DTP (wP) vaccines compared to the isotype control antibody treated mice (FIG. 2). The reduction in serum IgE indicates reduction of Th2 response and/or prevention or reduction in allergic reactions elicited by the vaccine.

Figure 7:
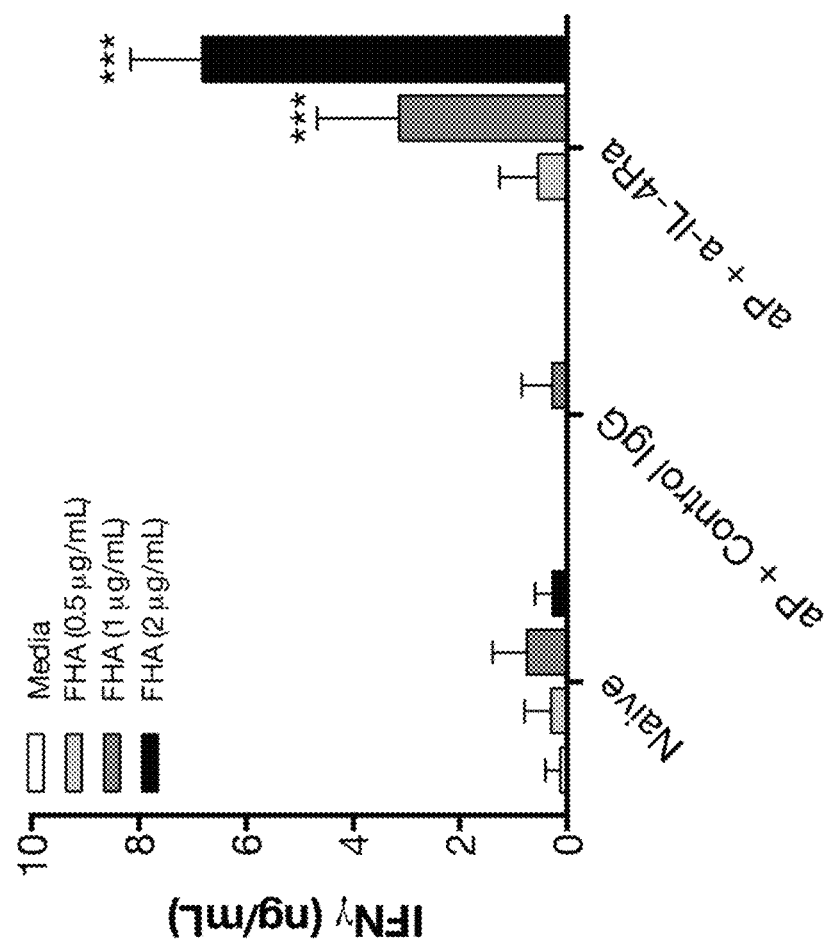
FIG. 7 shows that upon re-stimulation anti-IL-4Rα treatment in aP-immunized mice enhances FHA-specific interferon-gamma (IFN-γ) production by spleen cells. Results are the mean values for 4 mice per group. Two-way ANOVA statistical analysis was performed: * $p<0.001$
Figure 8A:
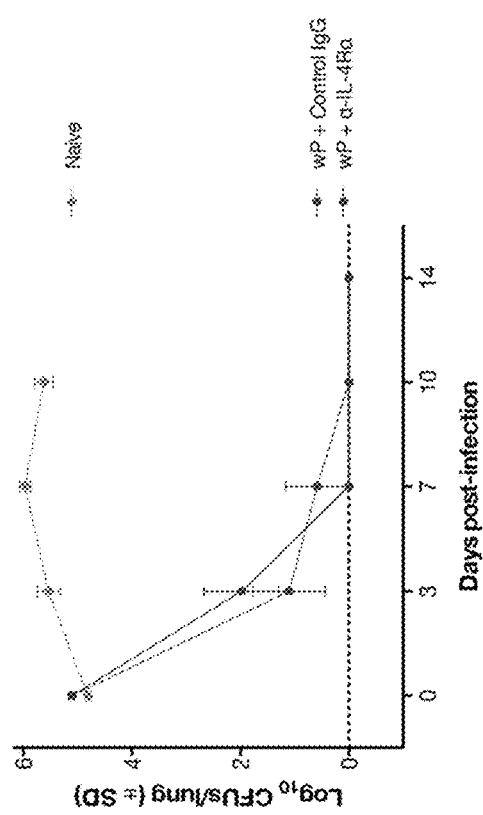
FIGS. 8A and 8B show numbers of colony forming units (CFUs) of B. pertussis per lung of mice immunized with two doses of either aP (FIG. 8A) or wP (FIG. 8B) and challenged with B. pertussis by aerosol exposure, as described in the study in Example 4. Results are the mean values for 4 to 8 mice per group at each time point [except for wP-immunized groups (B) on day 14, n=3]. *** $p<0.001$, aP+control IgG vs. aP+anti-IL-4Rα, by two-way ANOVA.
Figure 8B:
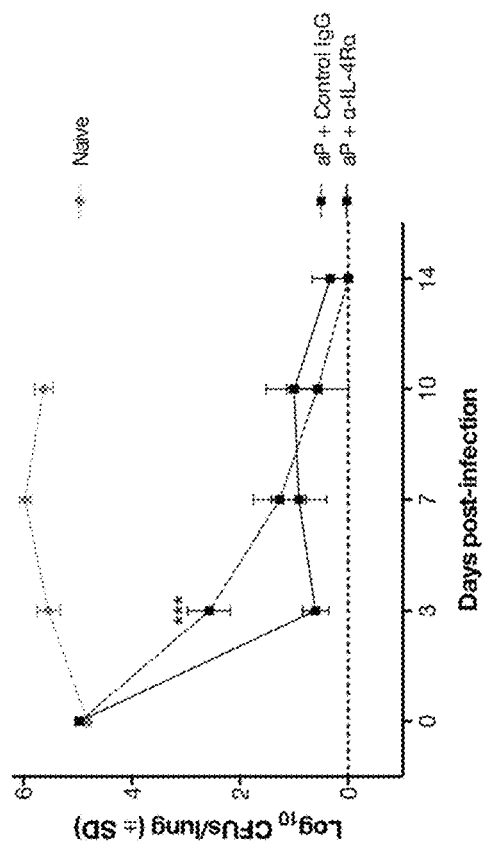
Figure 10:
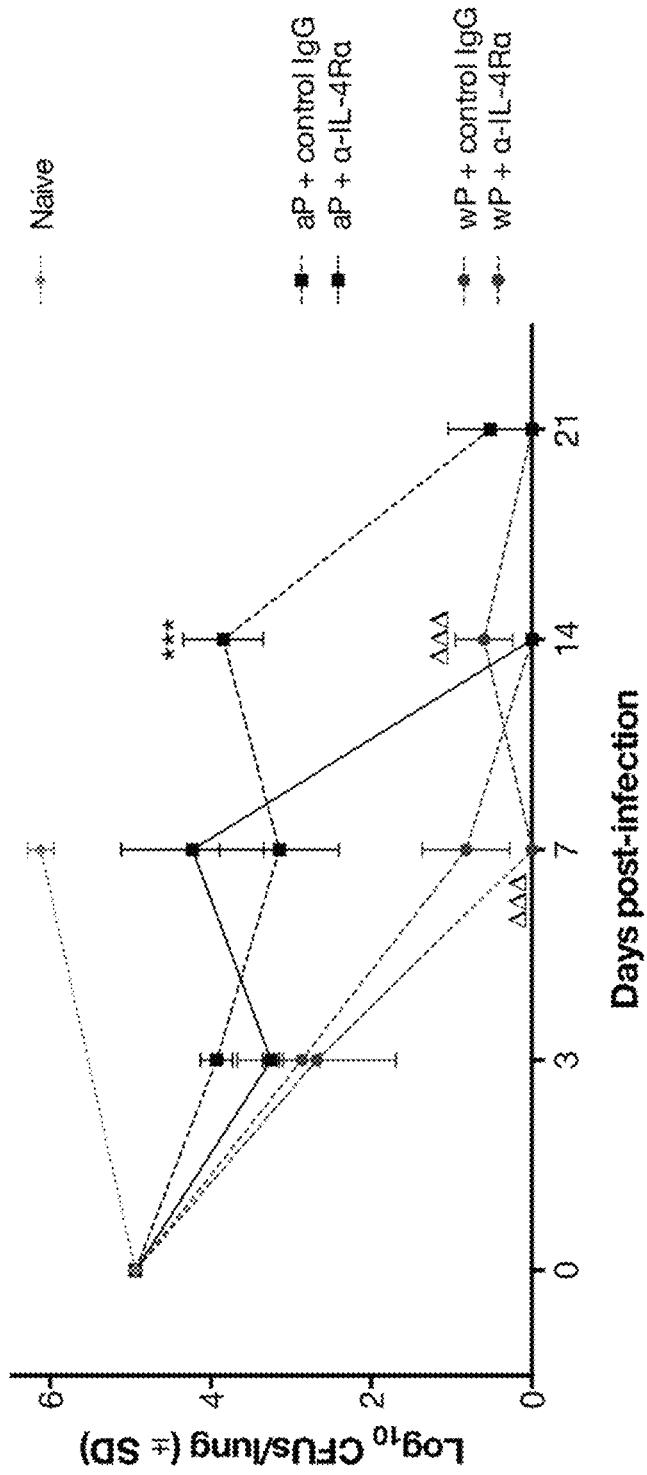
FIG. 10 shows numbers of colony forming units (CFUs) of B. pertussis per lung of mice immunized with a single dose of either aP or wP vaccine and challenged with B. pertussis by aerosol exposure, as described in the study in Example 5. Results are the mean values for 4 mice per group at each time point (except naïve group on day 7, n=3). *** $p<0.001$, aP+control IgG vs aP+anti-IL4Ra; ΔΔΔ $p<0.001$, aP+control IgG vs wP+control IgG, by two-way ANOVA.

Example 2: Effect of Anti-IL-4R Antibody Treatment on Antigen-Specific Serum IgG Antibodies in Mice Vaccinated with Pertussis Vaccine In this Example, the effect of anti-IL-4R antibody on antigen-specific serum antibodies induced by a whole cell pertussis (wP; Th1 immune response) or acellular pertussis (aP; Th2 immune response) vaccine was assessed using the *Bordetella pertussis* aerosol challenge infection model. C57BL/6 mice were immunized with either acellular pertussis (aP) vaccine [Adacel® TDaP (Sanofi Pasteur)] or whole cell pertussis (wP) (DTP, Serum Institute of India, Pune, India) on Days −42 and −14 before an aerosol challenge with a virulent strain of *B. pertussis* (Day 0). Treatments with an anti-mouse IL-4R antibody ("anti-IL-4Rα") or isotype control antibody commenced one week before initial immunization and continued weekly up to Day 7. The treatment regime is outlined in FIG. 1. The anti-IL-4Rα antibody used in this Example was an anti-mouse-IL-4R antibody comprising an HCVR with an amino acid sequence of SEQ ID NO: 11 and an LCVR with an amino acid sequence comprising SEQ ID NO: 12. Serum was collected from naive and immunized mice (4 mice per group per experiment) on the day of challenge. Antigen-specific serum antibodies were analyzed by ELISA using plate-bound heat-killed *B. pertussis* or FHA (5 mg/mL). Bound antibodies were detected using biotin-conjugated anti-mouse IgG, IgG1, IgG2a or IgG2c antibodies and peroxidase-conjugated streptavidin. Antibody levels are expressed as the mean endpoint titer determined by extrapolation of the linear part of the titration curve to 2 SD above the background value obtained with non-immune mouse serum.

Serum IgG specific for heat-killed *B. pertussis* were analyzed in wP-treated mice, while serum IgG specific for filamentous hemagglutinin (FHA) were analyzed for aP-treated mice. Immunization with aP or wP induced *B. pertussis*-specific IgG; total IgG titers were not changed by treatment with anti-IL-4Rα in aP-immunized mice, but a slight (albeit significant) increase in antigen-specific total IgG was observed in the wP-immunized mice (FIG. 3). Immunization with aP induced predominantly IgG1 anti-FHA antibodies (indicative of Th2 specific response), which were significantly reduced by anti-IL-4Rα treatment (FIG. 4). FHA-specific IgG2a and IgG2c titers (indicative of Th1 response) were significantly enhanced by treatment with anti-IL-4Rα; the titers were significantly higher in anti-IL-4Rα treated aP-immunized mice when compared with isotype control antibody treated aP-immunized mice (FIGS. 5 and 6). There was no significant difference in the heat killed *B. pertussis* (HK-BP)-specific IgG1 antibody titers between wP-immunized experimental groups, but there was a slightly significant increase in HK-BP-specific IgG2a and IgG2c titers in the group treated with anti-IL4Rα compared to isotype control antibody. This increase in IgG2a and IgG2c titers is not significant for individual experiments (each consisting of 4 mice per group), but is significant when results from multiple experiments are pooled.

Thus, anti-IL-4Rα treatment reduced the Th2 response induced by immunization with the aP vaccine and enhanced the Th1 response; this was reflected in a switching from serum IgG1 to IgG2a/c antibodies and a decrease in IgE concentrations.

Example 3: Effect of Anti-IL-4R Antibody on Antigen-Specific Production of Cytokines In this Example, the effect of anti-IL-4R antibody on antigen-specific production of cytokines following splenocyte ex vivo re-stimulation was studied using the *Bordetella pertussis* aerosol challenge infection model. C57BL/6 mice were immunized with either acellular pertussis (aP) vaccine [Adacel® TDaP (Sanofi Pasteur)] or whole cell pertussis (wP) (DTP, Serum Institute of India, Pune, India) on Days −42 and −14 before an aerosol challenge with a virulent strain of *B. pertussis* (Day 0). Treatments with an anti-mouse IL-4R antibody ("anti-IL-4Rα") or isotype control antibody commenced one week before initial immunization and continued weekly up to Day 7. The treatment regime is outlined in FIG. 1. The anti-IL-4Rα antibody used in this Example was an anti-mouse-IL-4R antibody comprising an HCVR with an amino acid sequence of SEQ ID NO: 11 and an LCVR with an amino acid sequence comprising SEQ ID NO: 12. Serum was collected from naive and immunized mice (4 mice per group per experiment) on the day of challenge (day 0). Antigen-specific cytokine production by spleen cells was analyzed by ELISA. Splenocytes were prepared from the spleens of mice by mechanical disruption of spleen tissue. Splenocytes were cultured with the indicated numbers or concentrations of heat-killed *B. pertussis* or purified FHA. Supernatants were removed after 72 h and IL-13, IL-17 and IFNγ concentrations were determined by ELISA.

Spleen cells from anti-IL-4Rα treated aP-immunized mice produced dose-dependent, significantly higher interferon gamma (IFNγ) in response to FHA stimulation than isotype control-treated mice (FIG. 7). IFNγ concentrations were detected in the spleen cells from all anti-IL-4Rα treated mice but at low concentrations in one out of four mice in the isotype control-treated aP-immunized mice. There was a trend towards reduced IL-13 in spleen cells from anti-IL-4Rα treated aP-immunized mice (data not shown). No FHA-specific IL-17 was detected. *B. pertussis*-specific IL-17 and IFNγ production by splenocytes from wP-immunized mice after re-stimulation was similar across all immunized groups (data not shown).

Example 4: Treatment with Anti-IL-4R Antibody Enhances the Efficacy of Pertussis Vaccine In this Example, the protective efficacy of anti-IL-4R antibody as an adjuvant for a whole cell pertussis (wP) or acellular pertussis (aP) vaccine was assessed using the *Bordetella pertussis* aerosol challenge infection model. C57BL/6 mice were immunized with either acellular pertussis (aP) vaccine [Adacel® TDaP (Sanofi Pasteur)] or whole cell pertussis (wP) (DTP, Serum Institute of India, Pune, India) on Days −42 and −14 before an aerosol challenge with a virulent strain of *B. pertussis* (Day 0). Treatments with an anti-mouse IL-4R antibody ("anti-IL-4Rα") or isotype control antibody commenced one week before initial immunization and continued weekly up to Day 7. The treatment regime is outlined in FIG. 1. The anti-IL-4Rα antibody used in this Example was an anti-mouse-IL-4R antibody comprising an HCVR with an amino acid sequence of SEQ ID NO: 11 and an LCVR with an amino acid sequence comprising SEQ ID NO: 12.

The colony forming units (CFU) levels per lung were assessed at 0, 3, 7, 10 and 14 days following *B. pertussis* challenge. Briefly, the course of infection was followed by performing CFU counts on lungs from groups of 4 mice at intervals after challenge. The lungs were aseptically removed and homogenized in 1 mL of sterile saline on ice. Undiluted and serially diluted homogenate from individual lungs was spotted in triplicate onto Bordet-Gengou agar plates and the number of CFU was calculated after 5 days incubation. The limit of detection was approximately 0.3 logo CFU per lung for groups of 4 mice at each time point.

Immunization with wP vaccine conferred the highest level of protection against aerosol challenge with live *B. pertussis* (FIG. 8). Anti-IL-4Rα treatment in the wP-immunized mice cleared the infection similar to isotype control treated wP-immunized mice. Anti-IL-4Rα treatment significantly enhanced the efficacy of the aP vaccine; mice immunized with aP vaccine and treated with anti-IL-4α had significantly less lung bacterial burden on day 3 when compared to isotype control treated mice. Anti-IL-4Rα treatment increased the efficacy of the aP vaccine by a third based on the areas under the clearance curves. The results from this Example suggest that IL-4R blockade in general is a useful therapeutic strategy for enhancing the protective effect of vaccines that elicit Th2 response.

Example 5: Administration of an Anti-IL-4R Antibody Enhances the Efficacy of a Single Dose of Vaccine In this Example, the *Bordetella pertussis* aerosol challenge infection model was used to assess the effect of anti-IL-4R antibody on the efficacy of a single dose of vaccine.

C57BL/6 mice were immunized once with either aP vaccine (Adacel® TDaP; Sanofi Pasteur), or wP vaccine (DTP, Serum Institute of India, Pune, India), three weeks before an aerosol challenge with a virulent strain of *B. pertussis*. Treatments with an anti-mouse IL-4R antibody ("anti-IL-4Rα") or isotype control antibody were commenced one week before immunization and continued weekly for the duration of the study. The treatment regime is outlined in FIG. 9. The anti-IL-4Rα antibody used in this Example was an antibody comprising an HCVR with an amino acid sequence of SEQ ID NO: 11 and an LCVR with an amino acid sequence comprising SEQ ID NO: 12.

The mice were then challenged with *B. pertussis*; lung CFUs were assessed at 0, 3, 7, 14 and 21 days post infection. Briefly, the course of infection was followed by performing CFU counts on lungs from groups of 4 mice at intervals after challenge. The lungs were aseptically removed and homogenized in 1 mL of sterile saline on ice. Undiluted and serially diluted homogenate from individual lungs was spotted in triplicate onto Bordet-Gengou agar plates and the number of CFU was calculated after 5 days incubation. The limit of detection was approximately 0.3 $\log_{10}$ CFU per lung for groups of 4 mice at each time point.

Immunization with the wP vaccine conferred the highest level of protection against aerosol challenge with live *B. pertussis* (FIG. 10), and the efficacy of the wP vaccine was not changed by anti-IL-4Rα treatment. Anti-IL-4Rα treatment significantly enhanced the efficacy of the aP vaccine, even when the vaccine was reduced to a single dose. Mice immunized with aP and treated with anti-IL-4α cleared the bacterial infection by day 14, whereas mice immunized with aP and treated with the isotype control still had 4 $\log_{10}$ bacteria on day 14 and had not completely cleared the infection by day 21. Anti-IL-4Rα treatment increased the efficacy of the aP vaccine by a third based on the areas under the clearance curves.

Anti-IL-4Rα significantly enhanced the efficacy of the aP vaccine, with the *B. pertussis* infection completely cleared by day 14. The one dose immunization protocol clearly illustrates the increased efficacy of the aP vaccine in combination with anti-IL4Rα treatment.

Example 6: Effect of Low Doses of Anti-IL-4R Antibody on the Th1 Response to Acellular Pertussis Vaccine In this Example, the effect of an anti-IL-4R antibody on serum total and antigen-specific antibodies induced by aP vaccine is assessed in a mouse model (as described in Examples 1 through 5 herein). C57BL/6 mice are immunized with acellular pertussis (aP) vaccine [Adacel® TDaP (Sanofi Pasteur)]. Mice are treated with an anti-mouse IL-4R antibody ("anti-IL-4Rα") or isotype control antibody before initial immunization (see below). The anti-IL-4Rα antibody used in this Example is an anti-mouse-IL-4R antibody comprising an HCVR with an amino acid sequence of SEQ ID NO: 11 and an LCVR with an amino acid sequence comprising SEQ ID NO: 12.

In a first experiment, 1 to 5 doses of the anti-IL-4R antibody are administered to animals in different groups at 25 mg/kg of the mouse body weight before vaccination with aP. One group of animals is additionally administered the anti-IL-4R antibody concurrent with the aP vaccine. One group of animals are additionally administered a booster dose of aP vaccine 4 weeks after the priming dose.

In another experiment, 1 to 5 doses of the anti-IL-4R antibody are administered to animals in different groups at 10 mg/kg of the mouse body weight before vaccination with aP. One group of animals is additionally administered the anti-IL-4R antibody concurrent with the aP vaccine. One group of animals are additionally administered a booster dose of aP vaccine 4 weeks after the priming dose.

In another experiment, 1 to 5 doses of the anti-IL-4R antibody are administered to animals in different groups at 1 mg/kg of the mouse body weight before vaccination with aP. One group of animals is additionally administered the anti-IL-4R antibody concurrent with the aP vaccine. One group of animals are additionally administered a booster dose of aP vaccine 4 weeks after the priming dose.

Serum is collected from naive and immunized mice 7 days and 21 days after vaccine administration. Antigen-specific serum antibodies are analyzed by ELISA using plate-bound heat-killed B. pertussis or FHA (5 mg/mL). Bound antibodies are detected using biotin-conjugated anti-mouse IgG, IgG1, IgG2a or IgG2c antibodies and peroxidase-conjugated streptavidin. Antibody levels are expressed as the mean endpoint titer determined by extrapolation of the linear part of the titration curve to 2 SD above the background value obtained with non-immune mouse serum.

It is expected that mice administered low doses of anti-IL-4R antibody prior to and/or concurrent with aP vaccine administration show a switch from serum IgG1 to serum IgG2a/c antibodies and a decrease in IgE concentration. Further, it is expected that even a single dose of anti-IL-4R antibody administered before vaccination with aP vaccine will lead to reduction of serum IgG1 levels and an increase in serum IgG2a/c levels and a decrease in IgE levels (i.e., switch from Th2 to Th1 response). Thus, anti-IL-4Rα treatment at low doses before and/or during vaccine administration reduces the Th2 response induced by immunization with the aP vaccine and enhances the Th1 response.

Example 7: IL-4R Blockade as an Adjuvant to aP Vaccine in Infant Baboon Model

Efficacy of an anti-IL-4R antibody as an adjuvant to acellular pertussis (aP) vaccine was evaluated in the clinically relevant infant baboon model (Warfel et al 2014, PNAS 111: 787). The anti-IL-4Rα antibody used in this Example was an anti-monkey-IL-4R antibody comprising an HCVR with an amino acid sequence of SEQ ID NO: 14 and an LCVR with an amino acid sequence comprising SEQ ID NO: 15 (hereinafter referred to as "mAb1").

The study design is outlined in Table 2.

TABLE 2

Vaccination and treatment study design

| Group | Vaccine | Vaccine schedule (months) | Treatment | Treatment schedule (months) | Number of animals |
|---|---|---|---|---|---|
| 1 | Unvaccinated | None | Placebo | 1, 2, 3, 4, 5, 6 | 2 |
| 2 | Unvaccinated | None | mAb1 | 1, 2, 3, 4, 5, 6 | 2 |
| 3 | aP | 2, 4, 6 | Placebo | 1, 2, 3, 4, 5, 6 | 4 |
| 4 | aP | 2, 4, 6 | mAb1 | 1, 2, 3, 4, 5, 6 | 4 |
| 5 | aP | 2, 4, 6 | mAb1 | 2, 4, 6 | 4 |
| 6 | wP | 2, 4, 6 | Placebo | 1, 2, 3, 4, 5, 6 | 4 |

Baboons are immunized with human doses of aP or wP, intramuscularly at 2, 4 and 6 months of age. For studies using aP, animals are vaccinated with Daptacel (Sanofi Pasteur) or Infanrix (GlaxoSmithKline). For studies using wP, animals are vaccinated with Triple Antigen (Serum Institute of India). Unvaccinated animals are age-matched.

All animals receive placebo or mAb1 subcutaneously at 1, 2, 3, 4, 5, and 6 months of age at a fixed dose, except for group 5 (Table 2) which receives mAb1 at 2, 4 and 6 months of age at a fixed dose. Whole blood is collected for serum and PBMCs at 1, 2, 3, 4, 5 and 6 months of age. Serum is evaluated for mAb1 levels and for pertussis-specific total IgG, IgG1, IgG4 and IgE levels. The animals are challenged by B. pertussis at 6 to 8 months of age.

It is expected that animals treated with anti-IL-4R antibody prior to vaccination with aP show an increase in pertussis-specific IgG1 levels (Th1-specific) and decrease in pertussis-specific IgG4 levels (Th2-specific). More importantly, animals treated with anti-IL-4R antibody prior to vaccination with aP vaccine are protected against disease upon B. pertussis challenge, as evidenced by faster clearance of bacterial infection from lungs.

Example 8: Clinical Trial of Acellular Pertussis Vaccine in Combination with Anti-IL-4R Antibody in Adolescents 10 to 15 Years of Age Efficacy of an anti-IL-4R antibody as an adjuvant is measured in a clinical trial in adolescents 10 to 15 years of age. One objective of the trial is to study the efficacy of the acellular pertussis vaccine (TDaP, Adacel®, Sanofi Pasteur) in combination with dupilumab. Dupilumab is a fully human anti-IL-4R antibody comprising a heavy chain comprising the amino acid sequence of SEQ ID NO: 9 and a light chain comprising the amino acid sequence of SEQ ID NO: 10; an HCVR/LCVR amino acid sequence pair comprising SEQ ID NOs: 1/2; and heavy and light chain CDR sequences comprising SEQ ID NOs: 3-8.

Study treatments include a 400 mg loading dose of dupilumab on day 1, followed by a 200 mg weekly dose; or a placebo double dose on day 1, followed by a weekly placebo dose. The study subjects receive an injection of 200 mg of dupilumab, or placebo, subcutaneously on days 8, 15, 22, 29, 36, and 43. On day 29, all subjects receive a single dose of TDaP (Adacel®, sanofi) vaccine. The subjects are monitored for an allergic reaction to the vaccine. Vaccine-specific serum Ig titers are checked 1, 4, 8, 16 and 24 weeks after vaccine injection.

The efficacy variables measured in this study include: (a) IgE titers; (b) FHA-specific total IgG titers; and (c) FHA-specific IgG1, and IgG4 titers.

The primary endpoint of the study is proportion of dupilumab-treated subjects with positive response to the vaccine on day 43. Positive response is defined as one or more of: (i) lower IgE titers in dupilumab-treated study subjects; (ii) higher vaccine-specific (e.g., anti-FHA) IgG4 titers in dupilumab-treated study subjects; and (iii) less number of adverse events (allergic reactions) in dupilumab-treated subjects as compared to placebo.

At the end of the study, the dupilumab-treated subjects have one or more of the following: (a) lower IgE titer as compared to placebo; (b) higher anti-FHA total IgG titer as compared to placebo; (c) lower IgG4 and higher IgG1 titers as compared to placebo. More than 50% of subjects in the study show positive response to the vaccine.

Example 9: Clinical Trial of Booster Doses of Acellular Pertussis Vaccine in Combination with Anti-IL-4R Antibody in Children Less than 10 Years of Age Efficacy of an anti-IL-4R antibody as an adjuvant is measured in a clinical trial in children less than 10 years of age. One objective of the trial is to study the efficacy of the acellular pertussis vaccine (DTaP, Sanofi Pasteur) in combination with dupilumab. Dupilumab is a fully human anti-IL-4R antibody comprising a heavy chain comprising the amino acid sequence of SEQ ID NO: 9 and a light chain comprising the amino acid sequence of SEQ ID NO: 10; an HCVR/LCVR amino acid sequence pair comprising SEQ ID NOs: 1/2; and heavy and light chain CDR sequences comprising SEQ ID NOs: 3-8.

Study treatments include a 50 mg loading dose of dupilumab on day 1, followed by a 25 mg dose; or a placebo double dose on day 1, followed by a placebo dose. The study subjects receive a subcutaneous injection of 25 mg of dupilumab (or placebo) biweekly on days 15, 29, 43, 57, 71, 85, 99, and 113; followed by secondary dose injections on days 141, 155, 162, 169, 176 and 183. All subjects receive a vaccine dose (DTaP) on day 43, followed by booster doses on days 113 and 176.

The subjects are monitored for an allergic reaction to the vaccine. Vaccine-specific serum Ig titers are checked 1, 4 and 8 weeks after each vaccine dose.

The efficacy variables measured in this study include: (a) IgE titers; (b) FHA-specific total IgG titers; and (c) FHA-specific IgG1, and -IgG4 titers.

The primary endpoint of the study is proportion of dupilumab-treated subjects with positive response to the vaccine on day. Positive response is defined as one or more of: (i) lower IgE titers in dupilumab-treated study subjects; (ii) higher vaccine-specific (e.g., anti-FHA) IgG1 titers in dupilumab-treated study subjects; and (iii) less number of adverse events (allergic reactions) in dupilumab-treated subjects as compared to placebo.

At the end of the study, the dupilumab-treated subjects have one or more of the following: (a) lower IgE titer as compared to placebo; (b) higher anti-FHA total IgG titer as compared to placebo; (c) lower IgG4 and higher IgG1 titers as compared to placebo. More than 50% of subjects in the study show positive response to the vaccine. More than 50% of dupilumab-treated subjects show higher IgG1 titers.

Example 10: Clinical Trial to Investigate Vaccine Responses in Adults with Atopic Dermatitis Treated with Dupilumab This was a 32-week, randomized, double-blind, placebo-controlled, parallel-group study assessing immunization responses to tetanus toxoid adsorbed Adacel® (tetanus, diphtheria, and acellular pertussis [TDaP]) and Menomune (meningococcal polysaccharide) vaccination in adults with moderate to severe AD who were treated with subcutaneously administered dupilumab. Eligible patients (194 patients) were randomized in a 1:1 ratio to receive dupilumab or placebo for 16 weeks. Randomization was stratified by baseline disease severity (IGA of moderate vs. severe). The treatment period was 16 weeks, with a subsequent follow-up period of 16 weeks.

Study Objectives

The primary objective of the study was to assess the T-cell dependent vaccine responses of patients with moderate to severe atopic dermatitis (AD) who were not adequately controlled on topical medication, who were treated with dupilumab 300 mg subcutaneous (SC) weekly.

The secondary objectives of the study were to assess: (i) T-cell independent vaccine responses of patients with moderate-to-severe AD who were treated with dupilumab 300 mg SC weekly; (ii) safety of concomitantly administered vaccines and SC dupilumab in patients with moderate-to-severe AD; and (iii) efficacy of dupilumab in patients with moderate to severe AD.

The primary endpoint in the study was the proportion of patients with a positive response to tetanus toxoid (the Adacel [TDaP] vaccine) at study week 16 (i.e., 4 weeks after immunization). A positive response was defined as a ≥4-fold increase from baseline in anti-tetanus IgG titers 4 weeks after administration of Adacel for patients with baseline titers ≥0.1 IU/mL or a titer of ≥0.2 IU/mL for patients with baseline titers of <0.1 IU/mL.

The secondary endpoints were: (i) proportion of patients with a positive response at study week 16 with positive response defined as a ≥2-fold increase from pre-vaccination baseline in anti-tetanus IgG titer for patients with pre-vaccination tetanus antibody titers ≥0.1 IU/ml or a titer of ≥0.2 IU/ml for patients with pre-vaccination titers of <0.1 IU/ml; (ii) Menomune response: an SBA titer of ≥8 for serogroup C (Immunological Basis for Immunization Series Module 15: Meningococcal Disease, World Health Organization 2010); (iii) proportion of patients who achieve Investigator's Global Assessment ([IGA] (0-1) at week 16; (iv) proportion of patients achieving at least 50% reduction in Eczema Area and Severity Index (EASI) scores at week 16; (v) proportion of patients achieving at least 75% reduction in Eczema Area and Severity Index (EASI) scores at week 16; (vi) change from baseline in maximum itch intensity Numerical Rating Scale (NRS) at week 16; (vii) change from baseline in BSA at week 16; (viii) change from baseline in the erythema of Global Individual Signs Score (GISS) at week 1; (ix) change from baseline in the infiltration/papulation of GISS at week 16; (x) change from baseline in the excoriations of GISS at week 16; (xi) change from baseline in the lichenification of GISS at week 16; (xii) change from baseline to week 16 in Patient Oriented Eczema Measure (POEM); (xiii) incidence of serious treatment-emergent adverse events (TEAEs) through week 20; (xiv) incidence of study drug discontinuation due to a TEAE through week 20; and (xv) incidence of skin-infections through week 20.

Study Design

The study consisted of a screening period, a treatment period and a follow-up period. Patients received a weekly injection of dupilumab from day 1 through week 15. After providing appropriate training on self-injection patients/caregivers self-injected dupilumab during weeks in which no clinic visit was scheduled (weeks 5, 6, 7, 9, 10, 11, 13, 14, and 15). The site contacted the patient by telephone to conduct visits at weeks 5, 6, 7, 9, 10, 11, 13, 14, and 15. At week 12, patients received Adacel (TDaP) vaccine and Menomune vaccine. The response to the vaccinations (anti-tetanus IgG titers and the serum bactericidal antibody (SBA) titers to meningococcal serogroups) was assessed 4 weeks later.

Patients who did or did not use emollients, mild to higher potency topical corticosteroids, and/or topical calcineurin inhibitors were potentially eligible for enrollment. Patients received treatment with topical AD therapies and/or with low-dose systemic corticosteroids (10 mg prednisone or its equivalent) at any time during the study, and could continue study drug. A single course of high-dose systemic corticosteroids (any steroid dose >10 mg prednisone or its equivalent) was used as rescue medication for up to 14 days after initiation and completed from day 1 through week 10 during the study, but study drug was temporarily discontinued during this time. Patients treated with high-dose systemic corticosteroids for AD could re-initiate study drug 5 halflives after the systemic corticosteroid was stopped, as long as the patient had no ongoing clinically significant adverse events (AEs) associated with the specific immunosuppressant, and after consultation and agreement with the medical monitor. After week 10 through week 16, use of high-dose systemic corticosteroids were prohibited.

For the dupilumab cohort, patients received loading dose of 600 mg SC on day 1, followed by 300 mg qw from week 1 through week 15.

For the placebo cohort, patients received a loading dose SC on day 1 followed by weekly SC dose of placebo from week 1 through week 15.

Adacel (TDaP) vaccine: Patients were vaccinated with Adacel (TDaP) vaccine IM at week 12.

Menomune vaccine: Patients were vaccinated with Menomune vaccine SC at week 12.

Adacel (Tdap) manufactured by Sanofi Pasteur was provided in prefilled syringes. Each 0.5 mL dose contained 5 Lf (flocculation units) tetanus toxoid (T), 2 Lf diphtheria toxoid (d), and acellular pertussis antigens (2.5 μg detoxified pertussis toxin, 5 μg filamentous hemagglutinin [FHA], 3 μg pertactin [PRN], 5 μg fimbriae types 2 and 3 [FIM]). Other ingredients per 0.5 mL dose included 1.5 mg aluminum phosphate (0.33 mg aluminum) as the adjuvant, ≤5 μg residual formaldehyde, <50 ng residual glutaraldehyde and 3.3 mg (0.6% v/v) 2 phenoxyethanol (not as a preservative). The antigens are the same as those in DAPTACELR, Diphtheria and Tetanus Toxoids and Acellular Pertussis Vaccine Adsorbed (DTaP); however, Adacel (Tdap) vaccine is formulated with reduced quantities of diphtheria and detoxified pertussis toxin. Menomune manufactured by Sanofi Pasteur was provided as single dose vial for SC use. The diluent (0.6 mL) for the single dose presentation contained sterile, pyrogen-free distilled water without preservative. The diluent (6 mL) for the multidose presentation contained sterile, pyrogen-free distilled water and thimerosal, a mercury derivative, which was added as a preservative for the reconstituted vaccine.

Study Population

The target population included adults with moderate-to-severe AD whose disease was not adequately controlled with topical medications, including those who were not appropriate candidates for treatment with effective topical therapy.

Inclusion Criteria:

A patient had to meet the following criteria to be eligible for inclusion in the study: (1) male or female adults ages 18 to 64 years with Chronic AD (according to the American Academy of Dermatology Consensus Criteria, [Eichenfeld 2004]) that was present for at least 3 years before the screening visit; (2) Patients with documented recent history (within 6 months before the screening visit) of inadequate response to a sufficient course of outpatient treatment with topical AD medication(s), or for whom topical AD therapies were otherwise inadvisable (eg, because of side effects or safety risks); (3) Eczema Area and Severity Index (EASI) score ≥16 at the screening visit and the baseline visit; (4) Investigator's Global Assessment (IGA) score ≥3 (on the 0-4 IGA scale) at the screening and baseline visits; and (5) ≥10% body surface area (BSA) of AD involvement at the screening and baseline visit.

Note for criterion #2: Inadequate response was defined as failure to achieve and maintain remission or a low disease activity state (comparable to IGA 0=clear to 2=mild) despite treatment with a daily regimen of topical corticosteroids of medium to higher potency (±topical calcineurin inhibitor as appropriate), applied for at least 28 days or for the maximum duration recommended by the product prescribing information (eg, 14 days for super-potent topical corticosteroids), whichever was shorter. Patients with documented systemic treatment for AD in the past 6 months were also considered as inadequate responders to topical treatments, and were eligible for treatment with dupilumab after appropriate washout. Important side effects or safety risks were those that outweighed the potential treatment benefits and included intolerance to treatment, hypersensitivity reactions, significant skin atrophy, and systemic effects, as assessed by the investigator or by the patient's treating physician. Acceptable documentation included contemporaneous chart notes that recorded topical medication prescription and treatment outcome, or investigator documentation based on communication with patient's treating physician. If documentation was inadequate, potential patients were re-screened after such documentation was obtained (e.g., patients shown to fail a 28-day course of mid-to-higher potency topical corticosteroids [±topical calcineurin inhibitor]).

Patients were allowed to enter the study on or off emollients, topical corticosteroids+/−topical calcineurin inhibitors, but had to meet the following requirements: (i) patients treated with a topical AD agent(s) at baseline must have been on a stable regimen for at least 14 days or at least the maximum duration of treatment recommended by the prescribing information, whichever was less; and (ii) patients not treated with a topical AD agent(s) at baseline may not have used them within 7 days prior to the baseline visit.

Procedures and Assessments

The efficacy of dupilumab in this population was assessed by measurement of tetanus IgG titers and SBA titers to meningococcal serogroups, a quality of life (QOL) questionnaire, and patient-reported outcomes. Response to vaccines was assessed by measurement of tetanus IgG titers and SBA titers to meningococcal serogroups.

Analysis Variables

The following demographic and baseline characteristics variables were summarized:

Demographic variables: age at screening (year), age group (<65, >=65), sex, ethnicity, race, baseline weight (kg), height (m), and BMI (kg/m2)

Baseline characteristics: (i) duration of AD disease, (ii) immunoglobulin isotypes (total IgG, IgM, IgA, and IgE), anti-tetanus IgG titers, and SBA titers for group A, C, Y, and W-135 polysaccharide antigens, (iii) Atopic Dematitis (AD)-related parameters including Pruritus Numerical Rating Scale (NRS), Investigator's Global Assessment (IGA) score, Eczema Area and Severity Index (EASI) score, Global Individual Signs Score (GISS), Body Surface Area (BSA) involvement of atopic dermatitis, patient global assessment of disease status, and Patient Oriented Eczema Measure (POEM). AD-related parameters have been described in US Patent Application Publication No. US2014/0072583, herein incorporated by reference in its entirety.

Statistical Plan

The full analysis set (FAS) included all randomized patients who received any study drug; it is based on the treatment allocated (as randomized). Efficacy endpoints were analyzed using the FAS. The safety analysis set (SAF) includes all randomized patients who received any study drug; it is based on the treatment received (as treated). Treatment compliance/administration and all clinical safety variables were analyzed using the SAF. The responders to the tetanus vaccine at study week 16 were explored by comparison of proportions of positive responders between dupilumab and placebo using the Cochran-Mantel-Haenszel (CMH) test stratified by randomization strata (disease severity). A 90% CI was presented with an exploratory p-value. For continuous endpoints, a mixed-effect model with repeated measures (MMRM) was used. This model includes the factors (fixed effects) for treatment, randomization strata (disease severity), study visits, treatment-by-visit interaction, and relevant baseline value. Statistical inferences were derived from the MMRM. Least square mean and 90% CI was driven from the MMRM model and no p-value was provided.

Results

Demographics and baseline characteristics are presented in Tables 3-6.

TABLE 3

Demographic Characteristics of the study population

|  | Placebo (N = 97) | Dupilumab 300 mg (N = 97) | Total (N = 194) |
|---|---|---|---|
| Age (years) (SD) | 40 (14.0) | 39 (13.6) | 40 (13.8) |
| Ethnicity n (%) | | | |
| Not Hispanic or Latino | 84 (86.6%) | 81 (83.5%) | 165 (85.1%) |
| Hispanic or Latino | 13 (13.4%) | 15 (15.5%) | 28 (14.4%) |
| Not reported | 0 | 1 (1.0%) | 1 (0.5%) |
| Race n (%) | | | |
| White | 67 (69.1%) | 60 (61.9%) | 127 (65.5%) |
| Black | 17 (17.5%) | 23 (23.7%) | 40 (20.6%) |
| Asian | 11 (11.3%) | 12 (12.4%) | 23 (11.9%) |
| Native American | 0 | 1 (1.0%) | 1 (1.5%) |
| Other | 2 (2.1%) | 1 (1.0%) | 3 (1.5%) |
| Sex n (%) | | | |
| Male | 46 (47.4%) | 49 (50.5%) | 95 (49.0%) |
| Female | 51 (52.6%) | 48 (49.5%) | 99 (51.0%) |
| Height (cm) (SD) | 167.7 (11.31) | 169.0 (10.08) | 168.3 (10.71) |
| Weight (kg) (SD) | 81.4 (19.00) | 81.1 (19.08) | 81.3 (18.99) |
| BMI (kg/m2) (SD) | 29.0 (7.72) | 27.9 (5.64) | 28.5 (6.78) |

TABLE 4

Baseline Titers of Antibodies

|  | Placebo (N = 97) | Dupilumab 300 mg (N = 97) | Total (N = 194) |
|---|---|---|---|
| Total IgG (g/L) (SD) | 12.4 (3.4) | 12.2 (3.5) | 12.3 (3.4) |
| Total IgM (g/L) (SD) | 1.0 (0.6) | 1.0 (0.5) | 1.0 (0.6) |
| Total IgA (g/L) (SD) | 2.8 (1.2) | 2.5 (1.0) | 2.7 (1.1) |
| Total IgE (g/L) (SD) | 1275.7 (1298.2) | 1051.4 (1250.5) | 1157.1 (1273.5) |
| Anti-tetanus IgG titer IU/mL | 1.7 (1.9) | 1.5 (1.3) | 1.6 (1.6) |
| Serum bactericidal Ab (SBA) titer Mean (SD) | 132.5 (639.26) | 62.2 (252.70) | 97.5 (486.98) |

TABLE 5

Baseline Characteristics for AD-associated parameters

|  | Placebo (N = 97) | Dupilumab 300 mg (N = 97) | Total (N = 194) |
|---|---|---|---|
| Body Surface Area (BSA) | 49.3 (24.6) | 45.8 (23.0) | 47.5 (23.8) |
| Eczema Area and Severity Index (EASI) | 31.2 (13.8) | 29.0 (13.1) | 30.1 (13.4) |
| Investigator Global Assessment (IGA) score | 3.4 (0.5) | 3.4 (0.5) | 3.4 (0.5) |
| Patients with IGA score 3 | 60 (61.9%) | 58 (59.8%) | 118 (60.8%) |
| Patients with IGA score 4 | 37 (38.1%) | 39 (40.2%) | 76 (39.2%) |
| Weekly Peak Pruritus Numeric Rating Scale (NRS) | 7.3 (2.2) | 7.4 (2.2) | 7.3 (2.2) |
| Global Individual Signs score (GISS) Total score | 8.8 (1.8) | 8.8 (1.8) | 8.8 (1.8) |

TABLE 5-continued

Baseline Characteristics for AD-associated parameters

| | Placebo (N = 97) | Dupilumab 300 mg (N = 97) | Total (N = 194) |
|---|---|---|---|
| Patient Oriented Eczema Measure (POEM) score | 20.6 (5.6) | 21.5 (6.0) | 21.1 (5.8) |
| Patient Global Assessment of Disease Status | | | |
| Poor (1) | 35 (36.1%) | 40 (41.2%) | 75 (38.7%) |
| Fair (2) | 44 (45.4%) | 35 (36.1%) | 79 (40.7%) |
| Good (3) | 15 (15.5%) | 18 (18.6%) | 33 (17.0%) |
| Very Good (4) | 3 (3.1%) | 2 (2.1%) | 5 (2.6%) |
| Excellent (5) | 0 | 2 (2.1%) | 2 (1.0%) |

TABLE 6

Summary of AD medical history

| | Placebo QW (N = 97) | Dupilumab 300 mg QW (N = 97) | Total (N = 194) |
|---|---|---|---|
| Duration of Atopic Dermatitis (years) | | | |
| n | 97 | 97 | 194 |
| Mean (SD) | 27 (17.2) | 28 (15.0) | 28 (16.1) |
| Median | 26 | 26 | 26 |
| Min:Max | 4:60 | 3:60 | 3:60 |
| Chronic Atopic Dermatitis Diagnosis Age | 97 | 97 | 194 |
| Before the age of 5 years old | 47 (48.5%) | 58 (59.8%) | 105 (54.1%) |
| Between age 5 and 9 years | 13 (13.4%) | 8 (8.2%) | 21 (10.8%) |
| Between age 10 and 19 years | 15 (15.5%) | 12 (12.4%) | 27 (13.9%) |
| Between age 20 and 29 years | 6 (6.2%) | 4 (4.1%) | 10 (5.2%) |
| Between age 30 and 39 years | 4 (4.1%) | 3 (3.1%) | 7 (3.6%) |
| Age 40 years and above | 12 (12.4%) | 12 (12.4%) | 24 (12.4%) |
| Number (%) of Patients with a personal medical history of Atopic/Allergic Conditions | 97 | 97 | 194 |
| Atopic Dermatitis | 97 (100%) | 97 (100%) | 194 (100%) |
| Ad Flare/Skin Infection | 93 (95.9%) | 81 (83.5%) | 174 (89.7%) |
| Other Allergies | 70 (72.2%) | 65 (67.0%) | 135 (69.6%) |
| Allergic Rhinitis | 50 (51.5%) | 54 (55.7%) | 104 (53.6%) |
| Asthma | 54 (55.7%) | 51 (52.6%) | 105 (54.1%) |
| Food Allergy | 35 (36.1%) | 42 (43.3%) | 77 (39.7%) |
| Allergic Conjunctivitis | 20 (20.6%) | 22 (22.7%) | 42 (21.6%) |
| Hives | 29 (29.9%) | 21 (21.6%) | 50 (25.8%) |
| Immunosuppressant Therapy | 22 (22.7%) | 13 (13.4%) | 35 (18.0%) |
| Chronic Rhinosinusitis | 13 (13.4%) | 10 (10.3%) | 23 (11.9%) |
| Aspirin Sensitivity | 1 (1.0%) | 4 (4.1%) | 5 (2.6%) |
| Number (%) of Patients with a personal medical history of Atopic/Allergic Conditions | | | |
| Nasal Polyps | 6 (6.2%) | 4 (4.1%) | 10 (5.2%) |
| Surgery For Nasal Polyps | 2 (2.1%) | 3 (3.1%) | 5 (2.6%) |
| Eosinophilic Esophagitis | 1 (1.0%) | 0 | 1 (0.5%) |
| Number (%) of Patients with a family medical history of Atopic/Allergic Conditions | 68 | 68 | 136 |
| Atopic Dermatitis | 41 (42.3%) | 51 (52.6%) | 92 (47.4%) |
| Asthma | 32 (33.0%) | 31 (32.0%) | 63 (32.5%) |
| Allergic Rhinitis | 26 (26.8%) | 27 (27.8%) | 53 (27.3%) |
| Other Allergies | 28 (28.9%) | 21 (21.6%) | 49 (25.3%) |
| Food Allergy | 15 (15.5%) | 18 (18.6%) | 33 (17.0%) |
| Hives | 9 (9.3%) | 11 (11.3%) | 20 (10.3%) |
| Allergic Conjunctivitis | 8 (8.2%) | 10 (10.3%) | 18 (9.3%) |
| Chronic Rhinosinusitis | 5 (5.2%) | 7 (7.2%) | 12 (6.2%) |
| Nasal Polyps | 1 (1.0%) | 3 (3.1%) | 4 (2.1%) |
| Eosinophilic Esophagitis | 0 | 1 (1.0%) | 1 (0.5%) |

The proportion of patients with a positive response to tetanus toxoid at week 16 in the dupilumab treatment arm (83.3%) was similar to that in the placebo treatment arm (83.7%). A 90% CI of the difference between treatment groups was (−9.41%, 8.69%).

Secondary measures of response included: the proportion of patients with a positive response to tetanus vaccination defined as ≥2-fold increase in anti-tetanus IgG titers 4 weeks post-vaccination (week 16); and the proportion of patients with a positive response to Menomune defined as a serum bactericidal antibody (SBA) response to serogroup C of ≥8, 4 weeks post vaccination (week 16).

A similar proportion of patients in the dupilumab treated group (95.6%) achieved a ≥2-fold increase in anti-tetanus IgG titers compared to placebo-treated patients (94.6%). A uniform response to the menomune vaccine was also observed for both treatment groups; 86.7% of dupilumab-treated patients achieved a SBA >8 compared to 87.0% for the placebo-treated patients. 90% CIs of differences between treatment groups in tetanus toxoid (≥2-fold increase) and Menomune responses were (−4.29%, 6.27%) and (−8.54%, 7.96%), respectively. However, dupilumab-treated patients showed reduced toxicity associated with the tetanus toxoid (e.g., skin reactions), as compared to placebo.

The results of other secondary efficacy endpoints are presented in Table 7.

TABLE 7

Secondary Efficacy Endpoints (Week 16)

| | Placebo QW (N = 97) | Dupilumab 300 mg QW (N = 97) |
|---|---|---|
| Number (%) patients with IGA 0-1 | 10 (10.3%) | 43 (44.3%) |
| Difference in % (90% CI) | 34.0% (24.29%, 43.75%) | |
| Number (%) patients with EASI 50 | 31 (32.0%) | 70 (72.2%) |
| Difference in % (90% CI) | 40.2% (29.40%, 51.01%) | |
| Number (%) patients with EASI 75 | 19 (19.6%) | 52 (53.6%) |
| Difference in % (90% CI) | 34.0% (23.38%, 44.66%) | |
| Change in weekly peak NRS | −2.33 (0.267) | −4.46 (0.256) |
| LS mean difference (90% CI) | −2.13 (−2.74, −1.51) | |
| % change weekly peak NRS | −27.89 (4.256) | −60.79 (4.045) |
| LS mean difference (90% CI) | −32.89 (−42.54, −23.25) | |
| Number (%) patients with NRS reduction ≥3 | 26 (26.8%) | 55 (56.7%) |
| Difference in % (90% CI) | 29.9% (18.80%, 41.00%) | |
| Number (%) patients with NRS reduction ≥4 | 19 (19.6%) | 49 (50.5%) |
| Difference in % (90% CI) | 30.9% (20.27%, 41.59%) | |
| Change in BSA | −12.0 (2.15) | −30.0 (2.04) |
| LS mean difference (90% CI) | −18.0 (−22.9, −13.2) | |
| Change in POEM | −4.8 (0.73) | −13.3 (0.70) |
| LS mean difference (90% CI) | −8.5 (−10.2, −6.9) | |
| Change in GISS | −1.8 (0.29) | −4.2 (0.28) |
| LS mean difference (90% CI) | −2.5 (−3.1, −1.8) | |

All P < 0.0001

Additional analyses include total IgE, and FHA-specific IgG1 and IgG4 titers in placebo- and dupilumab-treated patients. It is expected that dupilumab-treated patients have lower IgE titers, as compared to placebo.

Patients on dupilumab had significantly lower total IgE as compared to placebo (Table 8).

TABLE 8

Total IgE levels from baseline to end of study

| | Placebo QW (N = 79) | Dupilumab 300 mg QW (N = 76) | P-value[a] |
|---|---|---|---|
| Baseline IU/mL (IQR) | 1886 (397:7200) | 798 (214:2784) | |
| Week 12 IU/mL (IQR) | 1943 (361:9000) | 468.5 (129:1366) | |
| Week 16 IU/mL (IQR) | 1679 (333:8700) | 363.5 (97.25:1172) | |
| Week 32 IU/mL (IQR) | 1754 (284:7900) | 323.5 (85.75:969.3) | |
| Percent change from baseline to week 32 (IQR) | −7.229% (−24.87:18.07) | −54.78% (−72.69:−46.58) | <0.0001 |

[a]percent IgE change between placebo- and dupilumab-treated groups was compared via Mann-Whitney t-test IgE levels in response to TDaP vaccine components [pertussis toxin (PT), pertussis pertactin (PRN) and tetanus toxoid (TT)] were analyzed. In addition to vaccine-specific IgE, two allergens were included in the analysis (Fel d 1; a cat allergen and Bet v 1; a birch allergen). Allergic antibody responses to allergen and TDaP antigens were assessed by measuring Fel d 1, Bet v 1, tetanus toxoid (TT), pertussis toxin (PT), and pertussis pertactin (PRN) IgE levels via a modified Luminex® antibody assay. Sera from week 12 (time of TDaP immunization) week 16 (end of treatment period) and week 32 (end of study) were treated with GullSORB™ and incubated with Fel d 1, Bet v 1, TT, PT, or PRN coated microspheres. Bound specific IgE levels were detected via an anti-hIgE antibody conjugated with R-phycoerythrin (PE) and reported as TDaP TT-, PT-, or PRN- or allergen Fel d 1- or Bet v 1-specific IgE Mean Fluorescent Intensity (MFI). Values three SD above the mean of a negative control serum were considered IgE positive for that respective TDaP antigen or allergen.

The IgE responses to Fel d 1 trended lower and the IgE responses to Bet v 1 were significantly lower in dupilumab treated individuals, especially at week 32 (end of study). Fifty-four and 12.1% of dupilumab-treated individuals versus 65.2% and 30.4% of placebo-treated individuals were positive for Fel d 1-specific IgE (p=0.067) and Bet v 1-specific IgE (p<0.001), respectively at week 32. The allergic status of the patients to these allergens was unknown.

Dupilumab- and placebo-treated patients had similar TDaP-specific IgE MFIs; however placebo-treated patients showed a higher frequency of eliciting a TDaP-specific IgE response. Table 9 shows TDaP-specific IgE seropositivity between placebo- and dupilumab-treated patients at week 12 (time of TDaP immunization) week 16 (end of treatment period) and week 32 (end of study).

TABLE 9

TDaP-specific IgE seropositivity in placebo-treated and dupilumab-treated patients from time of immunization to end of study

|  | Placebo (N = 69) | Dupilumab 300 mg QW (N = 74) | P-value[a] |
|---|---|---|---|
| Week 12 | | | |
| Number (%) IgE positive for 1 TDaP antigen | 13 (18.84%) | 11 (14.86%) | |
| Number (%) IgE positive for 2 TDaP antigens | 9 (13.04%) | 7 (9.46%) | |
| Number (%) IgE positive for 3 TDaP antigens | 12 (17.39%) | 5 (6.76%) | |
| Total number (%) TDaP IgE positive | 34 (49.27%) | 23 (31.08%) | 0.0398 |
| Week 16 | | | |
| Number (%) IgE positive for 1 TDaP antigen | 7 (10.14%) | 12 (16.22%) | |
| Number (%) IgE positive for 2 TDaP antigens | 17 (24.64%) | 6 (8.11%) | |
| Number (%) IgE positive for 3 TDaP antigens | 16 (23.19%) | 8 (10.81%) | |
| Total number (%) TDaP IgE positive | 40 (57.97%) | 26 (35.15%) | 0.0074 |
| Week 32 | | | |
| Number (%) IgE positive for 1 TDaP antigen | 14 (20.29%) | 9 (12.16%) | |
| Number (%) IgE positive for 2 TDaP antigens | 8 (11.59%) | 6 (8.11%) | |
| Number (%) IgE positive for 3 TDaP antigens | 23 (33.33%) | 13 (17.57%) | |
| Total number (%) TDaP IgE positive | 45 (65.21%) | 28 (37.83%) | 0.0014 |

[a]TDaP IgE positivity between placebo and dupilumab treated individuals were compared by Fishers exact test As shown in Table 9, the majority of dupilumab-treated patients (62.16%) were seronegative for vaccine-specific IgE as compared to placebo (34.78%) by end of study (week 32).

Overall, dupilumab-treated individuals have a significant decrease (−54.7% from baseline) in total IgE compared to placebo-treated individuals (−7.2%) by end of study (p=<0.0001). Dupilumab-treated patients were less likely to develop TDaP-specific IgE responses. By week 32 (end of study), 37.8% dupilumab-treated versus 65.22% placebo-treated patients developed TDaP-specific IgE antibodies (the majority of patients were TDaP IgE-positive for all three vaccine antigens measured).

FHA-specific IgG1 and IgG4 titers were determined at weeks 4, 16 and 32 in placebo- and dupilumab-treated patients. Patients on dupilumab showed significant increase in FHA-specific IgG1 at 4 weeks and 16 weeks post-vaccination, but no treatment-specific responses were observed. It was surmised that based on their ages, patients may have received a full course of wP during their childhood. If true, this indicated that there was a Th1 bias in wP-primed patients which was maintained into adulthood.

Safety

Treatment-emergent AEs (TEAEs, AEs that developed or worsened in severity compared to the baseline during the treatment and follow-up period) and Treatment Emergent Potentially Clinically Significant Values (PCSV) in laboratory variables, ECG and vital signs were studied. There were 3 serious TEAEs in 3 dupilumab patients (3.1%). There was one mycosis fungoides stage IV, one squamous cell skin carcinoma and one serum sickness-like reaction. There were no serious treatment emergent adverse events in placebo group. Incidence of treatment emergent adverse events was lower in dupilumab group compared to the placebo group, (55.7%, vs. 61.9%, respectively). A review of adverse events by MedDRA System Organ Class (SOC) showed no pattern suggestive of an adverse drug effect on a specific organ system. The most commonly reported SOCs was 'Infections and infestations' (32.0% for placebo, vs. 35.1% for dupilumab), 'General disorders and administration site conditions' (7.2% for placebo vs. 16.5% for dupilumab), 'Skin and subcutaneous tissue disorders' (16.5% for placebo vs. 7.2% for dupilumab), 'Respiratory, thoracic and mediastinal disorders' (10.3% for placebo vs. 7.2% for dupilumab), 'Gastrointestinal disorders' (5.2% for placebo vs. 11.3% for dupilumab). The most common TEAEs included Upper respiratory tract infection (14.4% for placebo vs. 11.3% for dupilumab), Dermatitis atopic (11.3% for placebo vs. 1.0% for dupilumab), and Nasopharyngitis (5.2% for placebo vs. 4.1% for dupilumab). The dupilumab-treated group showed lower incidence of injection site reactions, localized swelling or swelling of lymph nodes associated with vaccine injections, as compared to placebo.

Conclusions

Dupilumab did not suppress response of patients to T-cell dependent vaccine (dTap) and the T-cell independent vaccine (Menomune). Response of patients treated with dupilumab 300 mg qw to the T-cell dependent vaccine (dTap) and the T-cell independent vaccine (Menomune) were comparable to response of placebo treated patients. All secondary efficacy endpoints showed statistical significance favoring dupilumab group. Dupilumab 300 mg qw was safe and well tolerated. The safety profile of dupilumab appeared consistent with that seen from previous studies.

Example 11: Duration of Th1 vs. Th2 Response to Pertussis Vaccine in Human Subjects This Example examines the duration of Th1/Th2 response to pertussis vaccines in human subjects primed with whole-cell (wP) or acellular pertussis (aP) vaccine in childhood. Individuals primed with wP or aP vaccine are divided into 6 groups. Individuals primed with wP or aP are boosted with wP, aP or no vaccine (control). Antibody isotypes (total and antigen-specific IgG isotypes and IgE) are studied in the groups. An earlier study examined T cell responses in these individuals (Bancroft et al 2016; 304-305: 35-43).

It is expected that the wP-primed individuals show antibody isotypes specific to Th1 response (increase in antigen-specific serum IgG1 levels), whether boosted by aP or wP. Similarly, aP-primed individuals show antibody isotypes specific to Th2 response (increase in antigen-specific serum IgG4 levels) irrespective of aP/wP booster. This indicates that the response triggered in response to initial vaccination by aP (Th2 specific response) or to wP (Th1 specific response) persists through adulthood.

Based on the results, it is suggested to administer an IL-4R antagonist at the time of and/or before the priming dose. Individuals administered with aP vaccine are administered an anti-IL-4R antibody before and/or concurrent with aP vaccine to imprint a Th1 response at the time of initial vaccination.

Example 12: Comparison of Anti-IL-4R Antibody as an Adjuvant with Other Adjuvants This Example examines the efficacy of an anti-IL-4R antibody as an adjuvant as compared to other adjuvants. The anti-IL-4Rα antibody used in this Example is an anti-mouse-IL-4R antibody comprising an HCVR with an amino acid sequence of SEQ ID NO: 11 and an LCVR with an amino acid sequence comprising SEQ ID NO: 12 ("anti-IL-4Rα").

Mice are immunized with ovalbumin as a model antigen in combination with different adjuvants like alum, AS04, AS03, MF59 and anti-IL-4Rα. Serum total and antigen-specific antibodies are analyzed. It is expected that administration of anti-IL-4Rα boosts ovalbumin immunity and induces a Th1 response as compared to ovalbumin itself.

In another experiment, anti-IL-4Rα is administered in combination with ovalbumin and alum. It is known in the art that alum induces Th2 response. Here it is expected that administration of anti-IL4Rα acts as a specific immunological modulator/blocker to alum and leads to a switch in Th1 response.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for enhancing the efficacy or safety, or both of a vaccine comprising:
    (a) selecting a subject that is susceptible to a pertussis infection; and
    (b) administering a vaccine specific to the pertussis infection in combination with an IL-4R antagonist to the subject, wherein the IL-4R antagonist is an antibody or antigen-binding fragment thereof that binds IL-4Rα, and comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

2. The method of claim 1, wherein the IL-4R antagonist is administered before, after or concurrent with the vaccine.

3. The method of claim 2, wherein the vaccine is administered at an initial dose followed by one or more subsequent (booster) doses.

4. The method of claim 3, wherein one or more doses of the IL-4R antagonist are administered before each dose of the vaccine.

5. The method of claim 4 comprising administering a dose of the IL-4R antagonist concurrent with each dose of the vaccine.

6. The method of claim 2 comprising administration of one or more doses of the IL-4R antagonist before the vaccine followed by a dose of the IL-4R antagonist concurrent with the vaccine, optionally followed by one or more doses of the IL-4R antagonist.

7. The method of claim 6, wherein each dose of the IL-4R antagonist comprises 1-10 mg/kg of the subject's weight.

8. The method of claim 6, wherein each dose comprises 10-600 mg of the IL-4R antagonist.

9. The method of claim 1, wherein the pertussis vaccine is selected from the group consisting of whole-cell vaccine or acellular vaccine.

10. The method of claim 9, wherein the vaccine is acellular pertussis (aP) vaccine.

11. The method of claim 1, wherein the subject is allergic to the vaccine.

12. The method of claim 1, wherein enhancing the efficacy or safety, or both of a vaccine comprises at least one of the effects selected from the group consisting of prevention of infection and transmission of infectious disease, increase in the duration of resistance to pathogen infection, faster pathogen clearance from infected host, reduction in pathogen load in infected organ, increase in T helper 1 (Th1) type antigen-specific IgG isotype antibodies, reduction or abrogation of IgE elicited by the vaccine, reduction in T helper 2 (Th2) response elicited by the vaccine, reduction in Th2-type antigen-specific IgG isotype antibodies, and reduction in allergic response to the vaccine.

13. The method of claim 1, wherein the antibody or antigen-binding fragment thereof prevents the interaction of IL-4 or IL-13, or both with a type 1 or type 2 IL-4 receptor.

14. The method of claim 13, wherein the antibody or antigen-binding fragment thereof prevents the interaction of IL-4 with both type 1 and type 2 IL-4 receptors.

15. The method of claim 1, wherein the antibody or antigen-binding fragment comprises a heavy chain variable region (HCVR) comprising the amino acid sequence of SEQ ID NO: 1 and a light chain variable region (LCVR) comprising the amino acid sequence of SEQ ID NO: 2.

16. The method of claim 1, wherein the IL-4R antagonist is dupilumab or a bioequivalent thereof.

17. The method of claim 7, wherein each dose of the IL-4R antagonist comprises 1 mg/kg, 2 mg/kg, 3 mg/kg, 5 mg/kg or 6 mg/kg of the subject's weight.

18. The method of claim 8, wherein each dose comprises 200 mg or 300 mg of the IL-4R antagonist.

19. The method of claim 8, wherein each dose comprises 100 mg of the IL-4R antagonist.

20. The method of claim 6, wherein the IL-4R antagonist is administered once a week, once every 2 weeks, once every 3 weeks, or once every 4 weeks.

21. The method of claim 1, wherein the IL-4R antagonist is administered subcutaneously.

* * * * *

```
                        SEQUENCE LISTING

<160> NUMBER OF SEQ ID NOS: 15

<210> SEQ ID NO 1
<211> LENGTH: 124
<212> TYPE: PRT
<213> ORGANISM: Artificial Sequence
<220> FEATURE:
<223> OTHER INFORMATION: HCVR

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: LCVR

<400> SEQUENCE: 2

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Leu Tyr Ser
                20                  25                  30

Ile Gly Tyr Asn Tyr Leu Asp Trp Tyr Leu Gln Lys Ser Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 3
<211> LENGTH: 8
<212> TYPE: PRT
<213> ORGANISM: Artificial Sequence
<220> FEATURE:
<223> OTHER INFORMATION: HCDR1

<400> SEQUENCE: 3

```
Gly Phe Thr Phe Arg Asp Tyr Ala
1               5
```

<210> SEQ ID NO 4
<211> LENGTH: 8
<212> TYPE: PRT
<213> ORGANISM: Artificial Sequence
<220> FEATURE:
<223> OTHER INFORMATION: HCDR2

<400> SEQUENCE: 4

```
Ile Ser Gly Ser Gly Gly Asn Thr
1               5
```

<210> SEQ ID NO 5
<211> LENGTH: 18
<212> TYPE: PRT
<213> ORGANISM: Artificial Sequence
<220> FEATURE:
<223> OTHER INFORMATION: HCDR3

<400> SEQUENCE: 5

```
Ala Lys Asp Arg Leu Ser Ile Thr Ile Arg Pro Arg Tyr Tyr Gly Leu
1               5                   10                  15

Asp Val
```

<210> SEQ ID NO 6
<211> LENGTH: 11
<212> TYPE: PRT
<213> ORGANISM: Artificial Sequence
<220> FEATURE:
<223> OTHER INFORMATION: LCDR1

<400> SEQUENCE: 6

```
Gln Ser Leu Leu Tyr Ser Ile Gly Tyr Asn Tyr
1               5                   10
```

<210> SEQ ID NO 7
<211> LENGTH: 3
<212> TYPE: PRT
<213> ORGANISM: Artificial Sequence
<220> FEATURE:
<223> OTHER INFORMATION: LCDR2

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: LCDR3

<400> SEQUENCE: 8

Met Gln Ala Leu Gln Thr Pro Tyr Thr
1               5

<210> SEQ ID NO 9
<211> LENGTH: 451
<212> TYPE: PRT
<213> ORGANISM: Artificial Sequence
<220> FEATURE:
<223> OTHER INFORMATION: HC
     aa1-124: HCVR
     aa125-451: HC constant

<400> SEQUENCE: 9

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

```
Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450

<210> SEQ ID NO 10
<211> LENGTH: 219
<212> TYPE: PRT
<213> ORGANISM: Artificial Sequence
<220> FEATURE:
<223> OTHER INFORMATION: LC
      aa1-112: LCVR
      aa113-219: LC constant

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
```

```
                        145                 150                 155                 160
Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 11
<211> LENGTH: 117
<212> TYPE: PRT
<213> ORGANISM: Artificial Sequence
<220> FEATURE:
<223> OTHER INFORMATION: mouse Ab HCVR

<400> SEQUENCE: 11

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asp Tyr
            20                  25                  30

Asn Ile His Trp Val Lys Gln Ser His Gly Lys Ser Leu Glu Trp Ile
        35                  40                  45

Gly Tyr Ile Tyr Pro Asn Asn Gly Asp Asn Gly Tyr Asn Gln Lys Phe
    50                  55                  60

Arg Gly Lys Ala Thr Leu Thr Val Asp Lys Ser Ser Ser Thr Ala Tyr
65                  70                  75                  80

Met Glu Leu Arg Ser Leu Thr Ser Asp Asp Ser Ala Val Tyr Tyr Cys
                85                  90                  95

Ala Arg Gly Arg Leu Arg Tyr Phe Asp Val Trp Gly Thr Gly Thr Thr
            100                 105                 110

Val Thr Val Ser Ser
        115

<210> SEQ ID NO 12
<211> LENGTH: 111
<212> TYPE: PRT
<213> ORGANISM: Artificial Sequence
<220> FEATURE:
<223> OTHER INFORMATION: mouse Ab LCVR

<400> SEQUENCE: 12

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly His Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Leu Asp
65                  70                  75                  80

Pro Val Glu Ala Asp Asp Ala Ala Thr Tyr Tyr Cys Gln Gln Tyr Asn
                85                  90                  95

Glu Asp Pro Pro Thr Phe Gly Ser Gly Thr Lys Leu Glu Ile Lys
            100                 105                 110
```

<210> SEQ ID NO 13
<211> LENGTH: 207
<212> TYPE: PRT
<213> ORGANISM: Artificial Sequence
<220> FEATURE:
<223> OTHER INFORMATION: hIL-4Ralpha

<400> SEQUENCE: 13

```
Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
    130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205
```

<210> SEQ ID NO 14
<211> LENGTH: 120
<212> TYPE: PRT
<213> ORGANISM: Artificial Sequence
<220> FEATURE:
<223> OTHER INFORMATION: HCVR monkey Ab

<400> SEQUENCE: 14

```
Glu Val Gln Leu Leu Glu Ser Gly Gly Gly Leu Leu Gln Pro Gly Gly
1               5                   10                  15

Ser Leu Arg Leu Ser Cys Ala Ala Ser Gly Ile Thr Phe Ser Thr Tyr
            20                  25                  30

Ala Met Ser Trp Val Arg Gln Ala Pro Gly Arg Gly Leu Glu Trp Val
        35                  40                  45

Ser Ala Ile Ser Gly Ser Gly Asp Ser Thr Tyr Ala Asp Ser Val
    50                  55                  60

Lys Gly Arg Phe Thr Ser Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ile Ala Ala Arg Pro His Trp Asn Phe Asp Leu Trp Gly
            100                 105                 110
```

```
Arg Gly Thr Leu Val Thr Val Ser
            115                 120

<210> SEQ ID NO 15
<211> LENGTH: 107
<212> TYPE: PRT
<213> ORGANISM: Artificial Sequence
<220> FEATURE:
<223> OTHER INFORMATION: LCVR monkey Ab

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Gly Val Tyr Tyr Cys Gln Gln Arg Ser Asp Trp Pro Leu
                85                  90                  95

Thr Phe Gly Gly Gly Thr Lys Val Glu Ile Lys
            100                 105
```